United States Patent
Cooymans et al.

(10) Patent No.: US 8,921,560 B2
(45) Date of Patent: Dec. 30, 2014

(54) INDOLES AS RESPIRATORY SYNCYTIAL VIRUS ANTIVIRAL AGENTS

(75) Inventors: Ludwig Paul Cooymans, Beerse (BE); Samuël Dominique Demin, Antwerp (BE); Lili Hu, Mechelen (BE); Tim Hugo Maria Jonckers, Edegem (BE); Pierre Jean-Marie Bernard Raboisson, Rosieres (BE); Abdellah Tahri, Anderlecht (BE); Sandrine Marie Helene Vendeville, Woluwe-Saint-Pierre (BE)

(73) Assignee: Janssen R&D Ireland (IE)

( * ) Notice: Subject to any disclaimer, the term of this patent is extended or adjusted under 35 U.S.C. 154(b) by 0 days.

(21) Appl. No.: 13/993,200

(22) PCT Filed: Dec. 16, 2011

(86) PCT No.: PCT/EP2011/073011
§ 371 (c)(1),
(2), (4) Date: Jun. 11, 2013

(87) PCT Pub. No.: WO2012/080447
PCT Pub. Date: Jun. 21, 2012

(65) Prior Publication Data
US 2013/0267555 A1 Oct. 10, 2013

(30) Foreign Application Priority Data
Dec. 16, 2010 (EP) .................................... 10195468

(51) Int. Cl.
| | | |
|---|---|---|
| C07D 471/04 | (2006.01) |
| C07D 403/06 | (2006.01) |
| C07D 513/02 | (2006.01) |
| C07D 515/02 | (2006.01) |
| A61K 31/437 | (2006.01) |
| A61P 31/12 | (2006.01) |

(52) U.S. Cl.
CPC ............ C07D 471/04 (2013.01); C07D 403/06 (2013.01)
USPC ........... 546/118; 546/113; 546/183; 514/303; 514/387; 514/414

(58) Field of Classification Search
USPC .......................................... 514/303; 546/118
See application file for complete search history.

(56) References Cited

U.S. PATENT DOCUMENTS

| | | | |
|---|---|---|---|
| 6,489,338 B2 | 12/2002 | Yu et al. | |
| 6,506,738 B1 * | 1/2003 | Yu et al. | ............................ 514/80 |
| 6,534,535 B1 * | 3/2003 | Zhu et al. | ....................... 514/414 |
| 6,919,331 B2 * | 7/2005 | Yu et al. | ....................... 514/223.2 |
| 7,361,657 B2 | 4/2008 | Janssens et al. | |
| 7,528,149 B2 | 5/2009 | Janssens et al. | |
| 2002/0016309 A1 * | 2/2002 | Yu et al. | ............................ 514/81 |
| 2004/0166137 A1 | 8/2004 | Lackey | |
| 2013/0261151 A1 * | 10/2013 | Cooymans et al. | ............ 514/303 |
| 2013/0267508 A1 * | 10/2013 | Cooymans et al. | ......... 514/222.2 |
| 2013/0267555 A1 | 10/2013 | Cooymans et al. | |
| 2013/0267556 A1 * | 10/2013 | Cooymans et al. | ............ 514/303 |
| 2013/0324527 A1 * | 12/2013 | Cooymans et al. | ......... 514/233.2 |

FOREIGN PATENT DOCUMENTS

| | | |
|---|---|---|
| WO | WO 98/01428 | 1/1998 |
| WO | WO 00/20400 | 4/2000 |
| WO | WO 01/95910 | 12/2001 |
| WO | WO 02/26228 | 4/2002 |
| WO | WO 03/053344 | 4/2003 |

OTHER PUBLICATIONS

Silverman; The Organic Chemistry of Drug Design and Drug Action, 2nd Ed, 2004, Elsevier, pp. 29 to 34.*
Beaulieu; Bioorg. Med. Chem. Lett. 16 (2006) 4987-4993.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Yu; Bioorganic & Medicinal Chemistry Letters 17 (2007) 895-901.*
Beaulieu; Bioorganic & Medicinal Chemistry Letters 16 (2006) 4987-4993.*
Giampieri; Antiviral Research 83 (2009) 179-185.*
Wermuth; Practice of Medicinal Chemistry 3rd ed, 2008, chapter 15, pp. 290-342.*
International Search Report—PCT/EP2011/073008, dated, Mar. 28, 2012.
International Search Report—PCT/EP2011/073011, dated, Mar. 27, 2012.
International Search Report—PCT/EP2011/073014, dated Mar. 28, 2012.
International Search Report—PCT/EP2011/073016, dated Mar. 27, 2012.
International Search Report—PCT/EP2011/073017, dated Mar. 28, 2012.

(Continued)

*Primary Examiner* — John Mabry
*Assistant Examiner* — Daniel Carcanague
(74) *Attorney, Agent, or Firm* — Mary A. Appollina

(57) ABSTRACT

Indoles having inhibitory activity on RSV replication and having the formula I

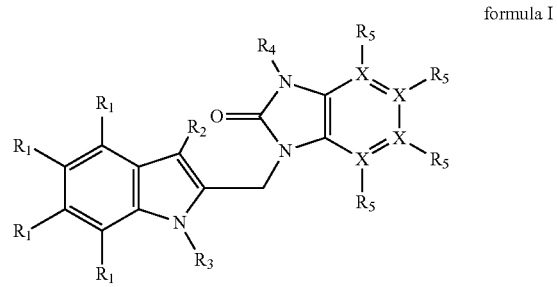

the prodrugs, N-oxides, addition salts, quaternary amines, metal complexes and stereochemically isomeric forms thereof; compositions containing these compounds as active ingredient and processes for preparing these compounds and compositions.

20 Claims, No Drawings

(56) References Cited

OTHER PUBLICATIONS

Banker, et al., Modern Pharmaceutics, 3 edition, 1996, pp. 451 and 596.

Wang, et al., "Respiratory Syncytial virus Fusion Inhibitors. Part 5: Optimization of Benzimidazole Substitution Patterns Towards Derivatives with Improved Activity", Biorganic and Medicinal Chemistry Letters, vol. 17, 2007, pp. 4592-4598.

Beaulieu, et al., "Improved Replicon Cellular Activity of Non-Nucleoside Allosteric Inhibitors of HCV NS5B Polymerase: From Benzimidazole to Indole Scaffolds", Biorganic & Medicinal Chemistry letters 16, 2006, pp. 4987-4993.

Goodman, et al, Biotransformation of Drugs:, The Pharmacological Basis of Therapeutics, 8th ed., 1992, pp. 13-15.

Giampieri, et al., "Antiviral Activity of Indole Derivatives", Antiviral Research, vol. 83, 2009, pp. 179-185.

Wyde, et al., AWY Dentiviral Research, vol. 38, 1998, pp. 31-42.

Wolff, et al., "Burger's Medicinal Chemistry, 5th edition", Part I, pp. 975-977, 1995.

Wermuth, "Molecular Variations Based on Isosteric Replacements", Practice of Medicinal Chemistry 3rd edition, 2008, pp. 290-342.

Yu, et al., "Respiratory Syncytial Virus Fusion Inhibitors. Part 4: Optimization for Oral Bioavailability" Biorganic & Medicinal Chemistry letters, vol. 17, 2007, pp. 895-901.

Silverman, et al., The Organic of Drug Design and Drug Action, pp. 29-34, 2004.

Pearce, et al., "E-Novo: An Automated Workflow for efficient Structure-Based Lead Optimization" J. Chem. Inf. Model, 2009, vol. 49, pp. 1797-1809.

Ito, et al., "A Medium-Term Rat Liver Bioassay for Rapid in Vivo Detection of Carcinogenic Potential of Chemicals" Cancer Science, 94(1) 2003, pp. 3-8.

Database Registry Chemical Abstracts Service, Columbus, Ohio, Assession No. RN 941045-14-3 and RN 931665-23-5.Entered STN: Jul. 4, 2007 and Apr. 22, 2007.

* cited by examiner

INDOLES AS RESPIRATORY SYNCYTIAL VIRUS ANTIVIRAL AGENTS

CROSS REFERENCE TO RELATED APPLICATIONS

This application is the national stage under 35 U.S.C. 371 of PCT Application No. PCT/EP2011/073011, filed Dec. 16, 2011, which application claims priority from European Patent Application No. EP 10195468.3, filed Dec. 16, 2010, the entire disclosures of which are hereby incorporated by reference in their entirety.

FIELD OF THE INVENTION

The invention concerns indoles having antiviral activity, in particular, having an inhibitory activity on the replication of the respiratory syncytial virus (RSV). The invention further concerns the preparation of these indoles, compositions comprising these compounds, and the compounds for use in the treatment of respiratory syncytial virus infection.

BACKGROUND

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue, that provides an aerosol treatment for serious RSV infection in hospitalized children. The aerosol route of administration, the toxicity (risk of teratogenicity), the cost and the highly variable efficacy limit its use. The other two drugs, Respi-Gam® (RSV-IG) and Synagis® (palivizumab), polyclonal and monoclonal antibody immunostimulants, are intended to be used in a preventive way. Both are very expensive, and require parenteral administration.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication. It would be particularly preferred to provide drugs against RSV replication that could be administered perorally.

A reference entitles "imidazopyridine and imidazopyrimidine antiviral agents" is WO 01/95910 which, in fact, relates to benzimidazole antiviral agents. Herein compounds are presented to have antiviral activity, yet with $EC_{50}$ values over a wide range of from 0.001 μm to as high as 50 μM (which does not normally represent the desired biological activity). Another reference, relating to substituted 2-methyl-benzimidazole RSV antiviral agents, in the same range of activities is WO 03/053344. Another related background reference ohm compounds in the same range of activities, is WO 02/26228 regarding benzimidazolone antiviral agents. A reference on structure-activity relations, in respect of RSV inhibition, of 5-substituted benzimidazole compounds is X. A. Wang et al., Bioorganic and Medicinal Chemistry Letters 17 (2007) 4592-4598.

It is desired to provide new drugs that have antiviral activity. Particularly, it would be desired to provide new drugs that have RSV replication inhibitory activity. Further, it would be desired to retrieve compound structures that allow obtaining antiviral biological activities of the order of magnitude in the stronger regions of the prior art (i.e. at the bottom of the above-mentioned range of up to 50 μM), and preferably at a level of about the most active, more preferably of even stronger activity, than the compounds disclosed in the art. A further desire is to find compounds having oral antiviral activity.

SUMMARY OF THE INVENTION

In order to better address one or more of the foregoing desires, the invention, in one aspect, presents antiviral indole compounds represented by formula I, a prodrug, N-oxide, addition salt, quaternary amine, metal complex, or a stereochemically isomeric form thereof;

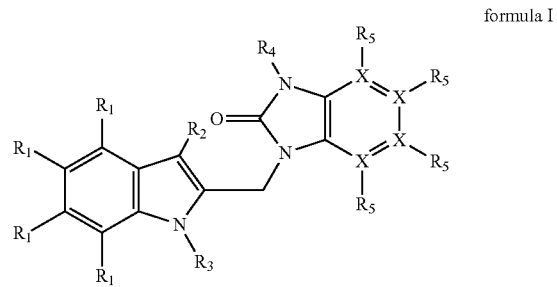

formula I wherein each X independently is C or N;
$R_1$ is selected from the group of H, halogen, $C_1$-$C_6$alkyl, $C_3$-$C_7$cycloalkyl, $C_1$-$C_6$alkoxy, $N(R_6)_2$, $CO(R_7)$, $CH_2NH_2$, $CH_2OH$, CN, C(=NOH)$NH_2$, C(=NOCH$_3$)$NH_2$, C(=NH)$NH_2$, $CF_3$, $OCF_3$, and $B(OH)_2$; B(O—$C_1$-$C_6$alkyl)$_2$;
$R_2$ is selected from the group consisting of H, halogen, $C_1$-$C_6$alkyl, $C_3$-$C_7$cycloalkyl, $C_1$-$C_6$alkoxy, and CO($R_7$);
$R_3$ is —(CR$_8$R$_9$)$_n$—R$_{10}$;
$R_4$ is selected from the group consisting of H, $C_1$-$C_{10}$alkyl, $C_3$—$C_7$cycloalkyl, $C_2$-$C_{10}$alkenyl, $SO_2$—$R_8$, $CH_2CF_3$, $SO_2CH_3$ or a 4 to 6 membered saturated ring containing an oxygen atom;
$R_5$ is present where X is C, and is selected from the group consisting of H, $C_1$-$C_6$alkyl, $C_3$-$C_7$cycloalkyl, $C_1$-$C_6$alkoxy, CO($R_7$), $CF_3$ and halogen;
$R_5$ is absent where X is N;
$R_6$ is selected from the group consisting of H, $C_1$-$C_6$alkyl, $COOCH_3$, and $CONHSO_2CH_3$;
$R_7$ is selected from the group consisting of OH, O($C_1$-$C_6$alkyl), $NH_2$, $NHSO_2N(C_1$-$C_6$alkyl)$_2$, $NHSO_2NHCH_3$, $NHSO_2(C_1$-$C_6$alkyl), $NHSO_2(C_3$-$C_7$cyclo-alkyl), and $N(C_1$-$C_6$-alkyl)$_2$, $NR_8R_9$, $NR9R_{10}$;

n is an integer from 2 to 6;
$R_8$ and $R_9$ are each independently chosen from H, $C_1$-$C_{10}$alkyl, $C_3$-$C_7$cycloalkyl or $R_8$ and $R_9$ taken together form a 4 to 6 membered aliphatic ring that optionally contains one or more heteroatoms selected from the group N, S, O;
$R_{10}$ is selected from the group consisting of H, $C_1$-$C_6$alkyl, OH, CN, F, $CF_2H$, $CF_3$, C(=NOH)$NH_2$, $CONR_8R_9$, $COOR_8$, $CONR_8SO_2R_9$, $CON(R_8)SO_2N(R_8R_9)$, $NR_8R_9$, $NR_8COOR_9$, $OCOR_8$, $NR_8SO_2R_9$, $SO_2NR_8R_9$, $SO_2R_8$ or a 4 to 6 membered saturated ring containing an oxygen atom.

In a preferred embodiment, $R_7$ is selected from the group consisting of OH, O($C_1$-$C_6$alkyl), $NH_2$, $NHSO_2N(C_1$-$C_6$alkyl$)_2$, $NHSO_2NHCH_3$, $NHSO_2(C_1$-$C_6$alkyl), $NHSO_2$($C_3$-$C_7$cycloalkyl), and N($C_1$-$C_6$-alkyl$)_2$;
$R_8$ and $R_9$ are each independently chosen from H, $C_1$-$C_{10}$alkyl, $C_3$-$C_7$cycloalkyl or $R_8$ and $R_9$ taken together form a 4 to 6 membered aliphatic ring that optionally contains a heteroatom selected from the group N, S, O;
$R_{10}$ is selected from the group consisting of H, $C_1$-$C_6$alkyl, OH, CN, F, $CF_2H$, $CF_3$, $CONR_8R_9$, $COOR_8$, $CONR_8SO_2R_9$, $CON(R_8)SO_2N(R_8R_9)$, $NR_8R_9$, $NR_8COOR_9$, $OCOR_8$, $NR_8SO_2R_9$, $SO_2NR_8R_9$, $SO_2R_8$ or a 4 to 6 membered saturated ring containing an oxygen atom.
Preferably, $R_4$ is selected from the group consisting of H, $C_1$-$C_{10}$alkyl, $C_3$-$C_7$cycloalkyl, $C_2$-$C_{10}$alkenyl, $SO_2$—$R_8$, or a 4 to 6 membered saturated ring containing an oxygen atom.

In another aspect, the invention relates to the foregoing compounds for use in the treatment of RSV infections in warm-blooded animals, preferably humans. In yet another aspect, the invention presents a method of treatment of viral RSV infections in a subject in need thereof, comprising administering to said subject an effective amount of a compound as defined above. In still another aspect, the invention resides in the use of a compound as defined above, for the manufacture of a medicament in the treatment of RSV infections.

In a further aspect, the invention relates to a pharmaceutical composition comprising a compound as defined above, and a pharmaceutically acceptable excipient.

In a still further aspect, the invention provides methods for preparing the compounds defined above.

DETAILED DESCRIPTION OF THE INVENTION

The molecules of formula I, in deviation from the prior art, have on one side (the left side in the formula as depicted) a substituted indole moiety. The invention, in a broad sense, is based on the judicious recognition that these substituted indole compounds generally possess an interesting RSV inhibitory activity. Moreover, these compounds enable access to anti-RSV activities at the higher regions (i.e. the lower end of the $EC_{50}$ values) of the range available in the aforementioned references. Particularly, on the basis of these compounds, molecular structures can be uncovered that even outperform the reference compounds in terms of biological activities.

The present invention will further be described with respect to particular embodiments and with reference to certain examples but the invention is not limited thereto but only by the claims. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

The term 'prodrug' as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, $8^{th}$ ed., McGraw-Hill, Int. Ed. 1992, "Biotransformation of Drugs", p. 13-15) describing prodrugs generally, is hereby incorporated. Prodrugs are characterized by a good aqueous solubility and bioavailability, and are readily metabolized into the active inhibitors in vivo.

As used herein $C_1$-$C_6$alkyl as a group or part of a group defines straight or branched chain saturated hydrocarbon radicals having from 1 to 6 carbon atoms such as methyl, ethyl, propyl, 1-methylethyl, butyl, pentyl, hexyl, 2-methylbutyl and the like.

$C_1$-$C_{10}$alkyl as a group or part of a group defines straight or branched chain saturated hydrocarbon radicals having from 1 to 10 carbon atoms such as the groups defined for $C_{1-6}$alkyl and heptyl, octyl, nonyl, 2-methylhexyl, 2-methylheptyl, decyl, 2-methylnonyl, and the like;

The term '$C_2$-$C_{10}$alkenyl' used herein as a group or part of a group is meant to comprise straight or branched chain unsaturated hydrocarbon radicals having at least one double bond, and preferably having one double bond, and from 2 to 10 carbon atoms such as ethenyl, propenyl, buten-1-yl, buten-2-yl, penten-1-yl, penten-2-yl, hexen-1-yl, hexen-2-yl, hexen-3-yl, 2-methylbuten-1-yl, hepten-1-yl, hepten-2-yl, hepten-3-yl, hepten-4-yl, 2-methylhexen-1-yl, octen-1-yl, octen-2-yl, octen-3-yl, octen-4-yl, 2-methylhepten-1-yl, nonen-1-yl, nonen-2-yl, nonen-3-yl, nonen-4-yl, nonen-5-yl, 2-methylocten-1-yl, decen-1-yl, decen-2-yl, decen-3-yl, decen-4-yl, decen-5-yl, 2-methylnonen-1-yl, and the like;

Whenever a $C_2$-$C_{10}$alkenyl group is linked to a heteroatom it preferably is linked via a saturated carbon atom.

$C_1$-$C_6$-alkoxy, as a group or part of a group defines an O—$C_1$-$C_6$alkyl radical, wherein $C_{1-6}$alkyl has, independently, the meaning given above.

$C_3$-$C_7$cycloalkyl is generic to cyclopropyl, cyclobutyl, cyclopentyl, cyclohexyl or cycloheptyl.

The term —$(CR_8R_9)_n$ used herein defines n repetitions of the $CR_8R_9$ subgroup, wherein each of these subgroups is independently defined.

The term halogen is generic to fluoro, chloro, bromo and iodo.

It should be noted that the radical positions on any molecular moiety used in the definitions may be anywhere on such moiety as long as it is chemically stable.

Radicals used in the definitions of the variables include all possible isomers unless otherwise indicated. For instance pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar term is meant to include the compounds of general formula (I), their prodrugs, N-oxides, addition salts, quaternary amines, metal complexes and stereochemically isomeric forms.

It will be appreciated that some of the compounds of formula (I) may contain one or more centers of chirality and exist as stereochemically isomeric forms.

The term "stereochemically isomeric forms" as used hereinbefore defines all the possible compounds made up of the same atoms bonded by the same sequence of bonds but having different three-dimensional structures which are not interchangeable, which the compounds of formula (I) may possess.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i e minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates, which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complexating properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

It will be appreciated that the compounds of the invention, with reference to the aforementioned left- and right-hand parts of formula I, present a wide variety of modification.

Without detracting from the overall scope of the invention, certain embodiments are discussed in more detail below.

In one preferred embodiment, $R_1$ is selected from the group consisting of H, halogen, $C_1$-$C_6$alkoxy, $CF_3$, and $OCF_3$. In a further preferred embodiment, $R_1$ in the para position to N—$R_3$ is selected from the group consisting of H, halogen and all other $R_1$ are H. In another preferred embodiment, halogen is bromo or chloro.

In another preferred embodiment, $R_3$ comprises a —$(CR_8R_9)_n$— chain wherein $R_8$ and $R_9$ are preferably H and n is 2-4. Preferably $R_{10}$ is selected from the group consisting of OH, F, $CF_2H$, $CF_3$, $SO_2R_8$, and CN. $R_8$ preferably is methyl.

In a preferred embodiment $R_4$ is $C_3$—$C_7$cycloalkyl, more preferably cyclopropyl.

In a preferred embodiment, and more preferably in conjunction with the other preferred embodiments, one X is N, and the other X's are C. In a most preferred embodiment, the one X that is N, is the X in para position to N—$R_4$.

Preferably at most one $R_5$ is selected from the group consisting of $C_1$-$C_6$ alkyl, $C_1$-$C_6$-alkoxy, halogen. Most preferably, all $R^5$ are H.

Preferred compounds are the compounds listed in table 1 below. Most preferred are compounds number 1, 2, and 3.

The compounds of formula I can be prepared by the methods described below, using synthetic methods known in the art of organic chemistry, or modifications and derivatisations that are familiar to those skilled in the art. The starting materials used herein are commercially available or may be prepared by routine methods known in the art such as those methods disclosed in standard reference books. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene and P. G. M. Wuts, Protective Groups in Organic Chemistry, John Wiley & Sons, 1999, which are hereby incorporated by reference.

Compounds of formula I, or their pharmaceutically acceptable salts, can be prepared according to the reaction schemes discussed herein below. Unless otherwise indicated, the substituent in the schemes are defined as above. Isolation and purification of the products is accomplished by standard procedures, which are known to a chemist of ordinary skill.

Scheme 1 illustrates a method for the preparation of compounds of formula I, where $R_1$ to $R_5$ and X are defined as above.

Referring to scheme 1, a compound of formula I can be synthesized by coupling 2-hydroxymethylene indole II-a with $N^3$-substituted 2-oxo-imidazopyridine or with $N^3$-substituted 2-oxo-imidazobenzene III with a method known in the art method such as a Mitsunobu reaction which uses azadiisopropyldicarboxylate and triphenyl phosphine in a suitable solvent such as DMF or THF. Alternatively, compound of formula I may be prepared by displacement of Y, which is a halide, preferably chlorine II-b, or a sulfonate such as mesylate II-c in the presence of a base such as sodium hydride, potassium carbonate or cesium carbonate in a suitable solvent such as DMF or THF.

Scheme 1

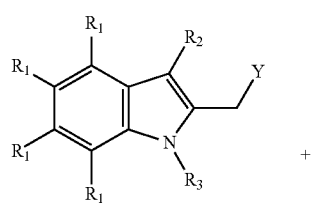

II-a Y = OH
II-b Y = Cl
II-c Y = SO₃Me

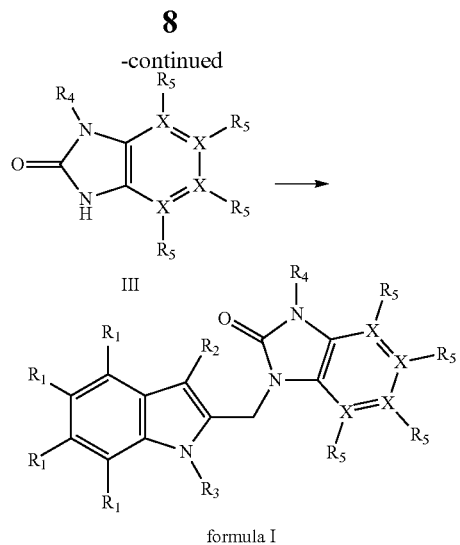

formula I

Preparation of Compound II-a

Starting materials IV used in this invention are commercially available, or can be synthesized, but not limited to, by methods known in the art such as Reissert synthesis or Fischer synthesis, reaction of such indoles with $R_3$-LG, where LG is a leaving group such as halide, preferably bromine, or sulfonate, in the presence of a base such as sodium hydride, potassium carbonate or cesium carbonate in a suitable solvent such as DMF or THF, gives compound V (scheme 2). The conversion of the alkyl ester of compound V to the alcohol II-a was carried out with metal hydride such as lithium aluminum hydride or sodium borohydride in a suitable solvent such as THF, methanol or ethanol.

Scheme 2

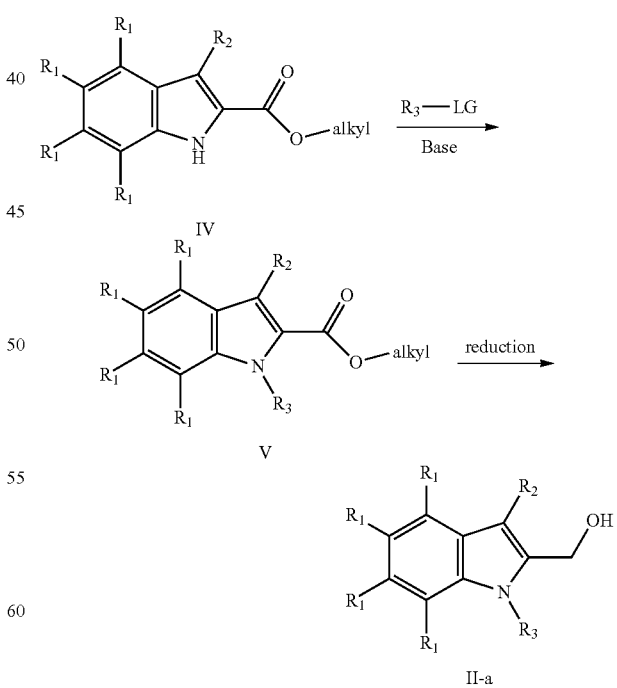

Treatment of the alcohol II-a with thionyl chloride provides 2-chloromethyl indole II-b. Alternatively, alcohol II-a may be transformed to the intermediate II-c by a reaction with methane sulfonyl chloride in the presence of an organic base such as triethyl amine or diisopropyl ethyl amine in a suitable solvent such dichloromethane (scheme 3).

Compounds III can be synthesized using the procedure depicted in scheme 4. Displacement of Z, which is a halide, preferably fluorine, or an alkoxy group, preferably methoxy, of nitro pyridine or of nitro aryl VI with an amine, in a suitable solvent such as THF or DMF, in the presence of an organic base such as triethyl amine or diisopropyl ethyl amine, gives compound VII. Reduction of the nitro group to the amine VIII can be done in a catalytic way using hydrogen in the presence of a catalyst such as palladium or platinum, in a suitable solvent such as methanol, or in a stoichiometric way using iron in the presence of ammonium chloride or tin chloride in the presence of concentrated hydrochloric acid. The cyclisation of the resulting diamine VIII using CDI, phosgene or triphosgene, in a solvent such as acetonitril or THF, provides $N^3$-substituted benzimidazolones III. Alternatively, compound of type III may be prepared starting from commercially available dianilines IX which can be cyclized by ring closure with CDI, phosgene or triphosgene yields intermediates of type X. Alkylation or sulfonylation of the urea nitrogen of X can be accomplished by a Mitsunobu reaction with commercially available alcohols, or by displacement of the chlorine in the compounds of type XI to yield compound of formula III.

Scheme 3

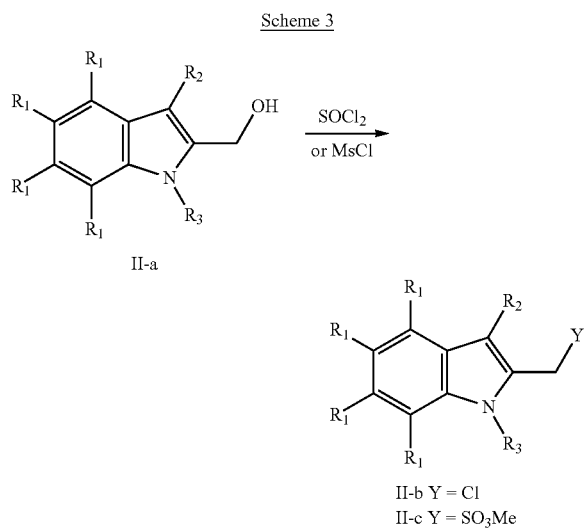

Scheme 4

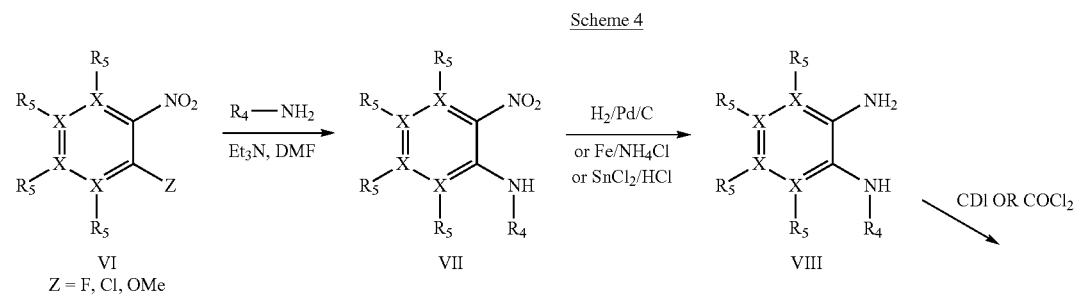

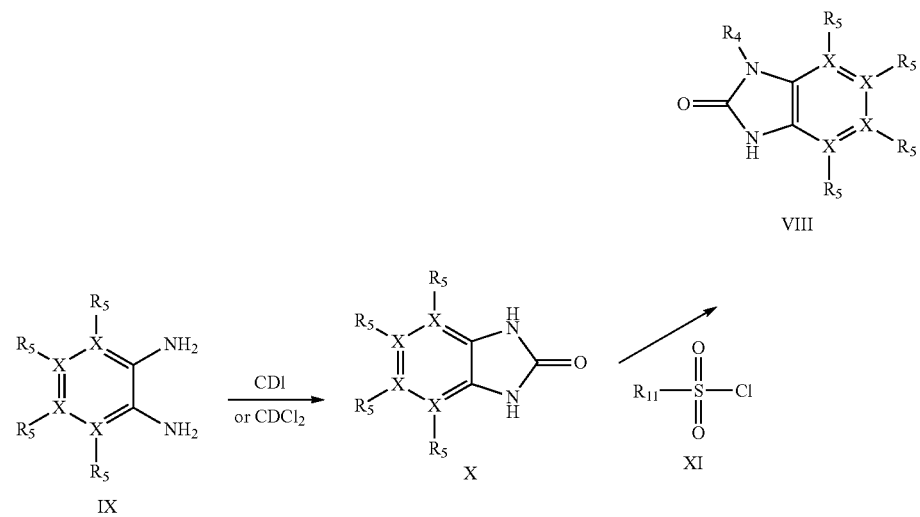

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylaxictically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any embodiment thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any embodiment thereof, their prodrugs, N-oxides, addition salts, quaternary amines, metal complexes and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any embodiment thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any embodiment thereof in the manufacture of a medicament for the treatment or the prevention of viral infections, particularly RSV infection.

The present invention furthermore relates to a method of treating a warm-blooded animal infected by a virus, or being at risk of infection by a virus, in particular by RSV, said method comprising the administration of an anti-virally effective amount of a compound of formula (I), as specified herein, or of a compound of any of the subgroups of compounds of formula (I), as specified herein.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The invention will hereinafter be illustrated with reference to the following, non-limiting examples.

Example 1

Synthesis of Intermediates

All the intermediates needed for the synthesis of targeted compounds of formula I are synthesised as described in the following scheme 5 to scheme 9.

Scheme 5: synthesis of 1-bromo-3-(methylsulfonyl)propane 5-c

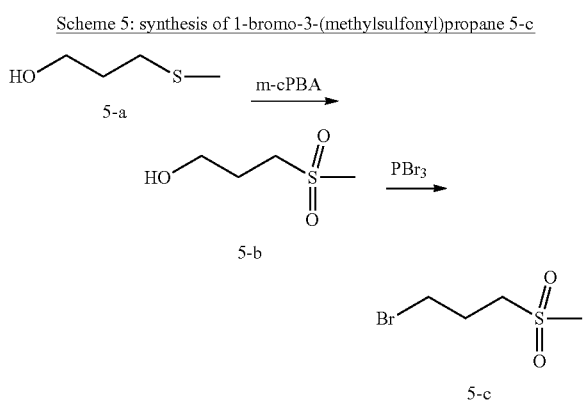

Step 1: Synthesis of 3-(methylsulfonyl)propan-1-ol 5-b

The alcohol 5-a (200 g, 1900 mmol) was dissolved in $CH_2Cl_2$ (2000 ml). The mixture was cooled to 0° C. The m-CPBA 85% in water (970 g, 5700 mmol) was added portion wise keeping the temperature between 0 to 5° C. After addition, the mixture was allowed to warm to 25° C. and stirred for 15 h. The mixture was filtered through a celite pad. The filtrate was purified by flash column (Eluent: petroleum ether:ethyl acetate=3:1 and then ethyl acetate: methanol=10:1) to yield the intermediate 5-b (75 g, 29%).

Step 2: Synthesis of 1-bromo-3-(methylsulfonyl)propane 5-c

The intermediate 5-b (75 g, 543 mmol) was dissolved in $CH_2Cl_2$ (750 ml). The mixture was cooled to 0° C. The phosphorus tribromide (53.6 ml, 570 mmol) was added drop wise keeping the temperature between 0 to 5° C. After addition, the mixture was allowed to warm to 25° C. and stirred for 15 h. The mixture was poured into ice-water. The separated organic layer was washed with brine (2×1500 mL), dried over $Na_2SO_4$, filtered and evaporated under vacuum to yield the title compound 5-c (77 g, 71%). $^1$H NMR (400 MHz, CHLOROFORM-d) δ ppm 2.25-2.40 (m, 2 H) 2.91 (s, 3 H) 3.1-3.2 (m, 2H) 3.5-3.6 (m, 2H).

Scheme 6: synthesis of tert-butyl(4-chlorobutoxy)dimethylsilane 6-b

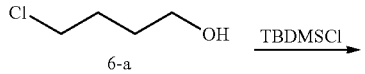

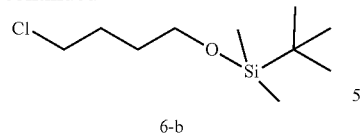
6-b

The alcohol 6-a (100 g, 920 mmol) was dissolved in CH₂Cl₂ (1000 ml) at room temperature. The mixture was cooled to 0° C. then Imidazole (81.5, 1200 mmol) and TBDMS-Cl (152 g, 1010 mmol) were added. The resulting mixture was stirred for 4 h at room temperature then filtered off. The filtrate was washed successively with 10% HCl and brine. The resulting solution was dried over MgSO₄, filtered then concentrated to yield the title compounds 6-b (100 g, 50%) as a colorless oil.

Scheme 7: synthesis of 1-cyclopropyl-1H-imidazol[4,5-c]pyridine-2(3H)-one 7-d

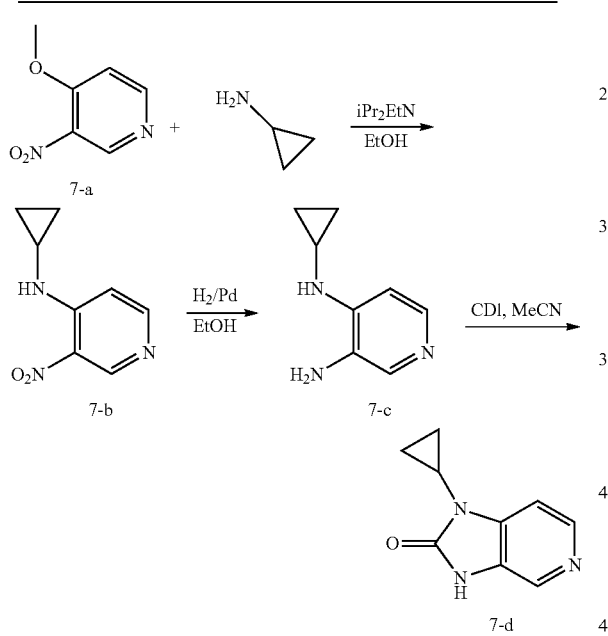

Step 1: Synthesis of N-cyclopropyl-3-nitropyridin-4-amine 7-b 4-methoxy-3-nitropyridine 7-a (CAS 31872-62-5) (200 g, 1300 mmol), cyclopropyl-amine (185.5 g, 3250 mmol) and diisopropyl ethyl amine (336 g, 2600 mmol) in dry ethanol (800 mL) were refluxed for 3 hours. The mixture was cooled to 0° C. The solid was collected by filtration. The filter cake was washed with cold ethanol (150 mL). The solid was dried to afford the title compound 7-b (167 g, 72% yield) as a white powder.

Step 2: Synthesis of N⁴-cyclopropylpyridin-3,4-diamine 7-c

Intermediate 7-b (167 g, 932 mmol) in ethanol (1400 mL) was hydrogenated (50 Psi) at 20° C. with wet 10% Pd/C (34 g) as a catalyst overnight. After uptake of H₂ (3 eq), the catalyst was filtered off and the filtrate was evaporated. The residue was washed with methyl terbutyl ether to afford the title compound 7-c (133 g, 95%) as a yellow powder.

Step 3: Synthesis of 1-cyclopropyl-1H-imidazo[4,5-c]pyridine-2(3H)-one 7-d

Carbonyldiimidazole (151.8 g, 936 mmol) was added to a solution of intermediate 7-c (133 g, 891.4 mmol) in CH₃CN (1800 mL) at 0° C. The reaction was allowed to warm to 10° C. and stirred for 1 h. The solid was collected by filtration and was washed with CH₃CN (200 ml) to afford the title compound 7-d (101 g, 65%) as a white powder.

Scheme 8: synthesis of 1-(oxetan-3-yl)-1H-imidazo[4,5-c]pyridine-2(3H)-one 8-d

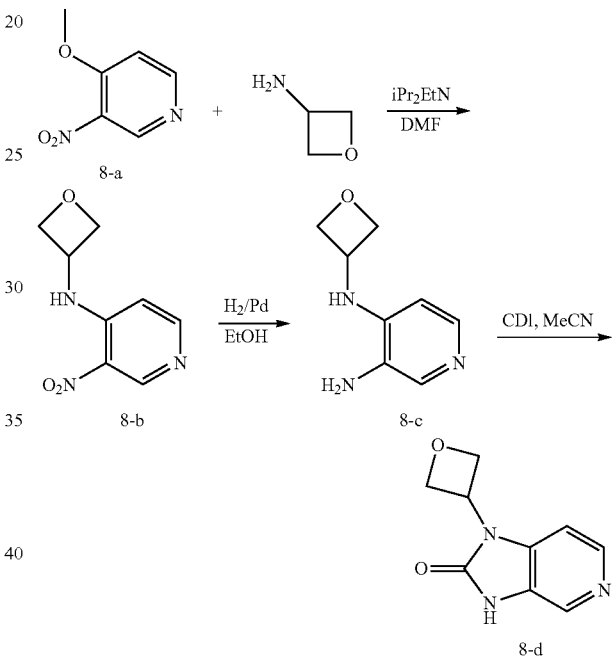

Compound 8-d was prepared in the same manner as compound 7-d using 3-aminooxetane as starting material.

Scheme 9: synthesis of 1-cyclopropyl-5-fluoro-1H-benzol[d]imidazol-2(3H)-one 9-d

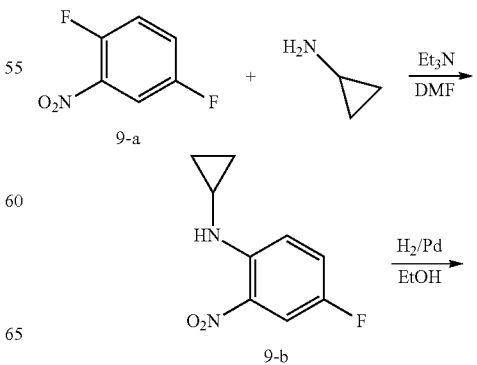

17

-continued

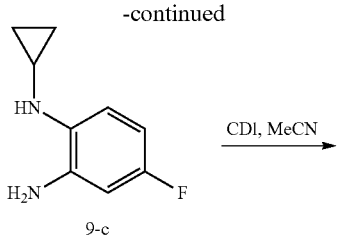

9-c

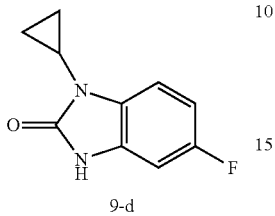

9-d

Step 1: Synthesis of N-cyclopropyl-4-fluoro-2-nitroaniline 9-b 1,4-difluoro-2-nitrobenzene 9-a (CAS 364-74-9) (15 g, 94.3 mmol) was dissolved in DMF (500 mL). Cyclopropyl amine (7 mL, 100 mmol) was added followed by triethylamine (30 mL, 217 mmol). The resulting mixture was stirred at room temperature overnight. The mixture was poured in water and extracted with dichloromethane dried over $MgSO_4$ and concentrated. The orange solid was purified by column chromatography using dichloromethane and methanol to yield intermediate 9-b (16 g, 86%) as an orange solid.

m/z=197 (M+H)$^+$. $^1$H NMR (400 MHz, CHLOROFORM-d) δ ppm 0.63-0.68 (m, 2H), 0.88-0.95 (m, 2 H), 2.54-2.55 (m, 1 H), 7.27-7.34 (m, 2 H), 7.84-7.90 (m, 1 H), 7.93-8.02 (m, 1 H)

Step 2: Synthesis of $N^1$-cyclopropyl-4-fluorobenzene-1,2-diamine 9-c

Intermediate 9-b (16 g, 82 mmol) in ethanol (200 mL) was hydrogenated at room temperature with wet 10% Pd/C as a catalyst overnight. After uptake of $H_2$ (3 eq), the catalyst was filtered off and the filtrate was evaporated. The residue was washed with ethanol to afford the title compound 9-c (12.8 g, 94%) as a white solid. m/z=167 (M+H)$^+$.

Step 3: Synthesis of 1-cyclopropyl-5-fluoro-1H-benzo[d]imidazol-2(3H)-one 9-d Carbonyldiimidazole (13.15 g, 81 mmol) was added to a solution of intermediate 9-c (12.8 g, 77.3 mmol) in $CH_3CN$ (150 mL) at 0° C. The reaction was allowed to warm up to room temperature and stirred for 4 hours. The solvent was removed, then the residue was purified by column chromatography using $CH_2Cl_2$/methanol to yield a light brown solid which was triturated in diethyl ether to yield compound 9-d (7.4 g, 50%) as a white solid. m/z=193 (M+H)$^+$.

$^1$H NMR (400 MHz, CHLOROFORM-d) δ ppm 0.99-1.08 (m, 2 H) 1.08-1.20 (m, 2 H) 2.89 (m, 1 H) 6.75-6.84 (m, 1 H) 6.87 (dd, J=8.53, 2.51 Hz, 1 H) 7.10 (dd, J=8.53, 4.27 Hz, 1 H) 10.33 (br. s., 1 H)

18

Example 2

Synthesis of 3-((5-bromo-1-(3-(methylsulfonyl)propyl)-1H-indol-2-yl)methyl)-1-cyclopropyl-1H-imidazo[4,5-c]pyridine-2(3H)-one 2

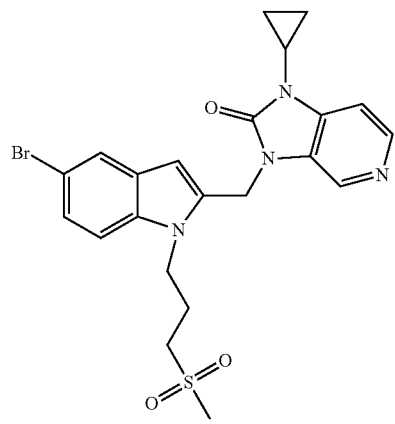

Step 1: Synthesis of ethyl 5-bromo-1-(3-(methylsulfonyl)propyl)-1H-indole-2-carboxylate 2-1

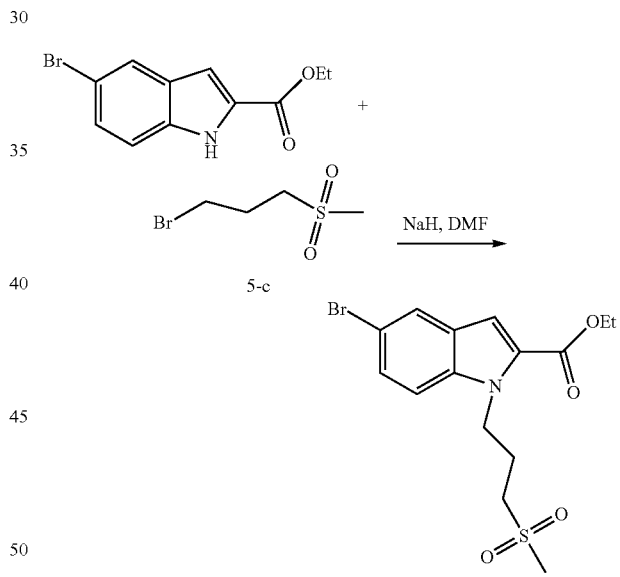

Ethyl 5-bromo-1H-indole-2-carboxylate (CAS 16732-70-0) (2.3 g, 8.6 mmol) was dissolved in DMF (50 mL). The mixture was stirred at room temperature, then sodium hydride 60% suspension in mineral oil (0.52 g, 12.8 mmol) was added. The resulting mixture was stirred at room temperature for 1 hour, then 1-bromo-3-(methylsulfonyl)propane 5-c (2.6 g, 12.8 mmol) was added. The resulting mixture was stirred at room temperature overnight. The mixture was poured in ice/water solution and extracted with ethyl acetate. The organic layer was dried over $MgSO_4$ and concentrated to yield a brown crude oil. The crude was purified by column chromatography using dichloromethane/methanol to yield the title compound 2-1 (3.2 g, 96%) as a white solid.

m/z=389 (M+H)$^+$.

Step 2: Synthesis of (5-bromo-1-(3-(methylsulfonyl)propyl)-1H-indol-2-yl)methanol 2-2

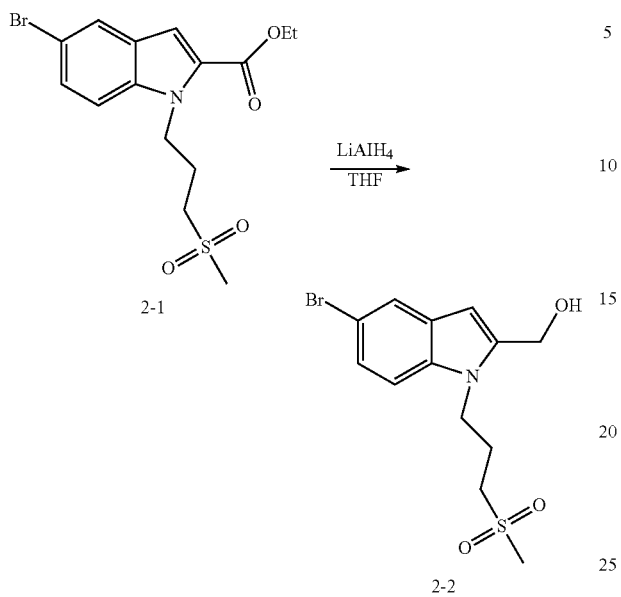

To a solution of intermediate 2-1 (3.2 g, 8.24 mmol) in THF (100 mL) was added at room temperature lithium aluminum hydride (2 M solution in THF, 5.2 mL, 10.4 mmol). The resulting mixture was stirred at room temperature overnight. The reaction mixture was quenched by addition of ethyl acetate and ethanol. The resulting mixture was poured in ice/water solution then filtered on celite. The aqueous layer was extracted with ethyl acetate (3×50 mL). The combined organic extracts were washed with brine (100 mL), dried over MgSO$_4$, filtered and concentrated under reduced pressure. The residue was purified by column chromatography using dichloromethane/methanol as the eluent. The product 2-2 was collected (2.5 g, 88%) as a white solid. m/z=347 (M+H)$^+$.

Step 3: Synthesis of 3-((5-bromo-1-(3-(methylsulfonyl)propyl)-1H-indol-2-yl)methyl)-1-cyclopropyl-1H-imidazo[4,5-c]pyridin-2(3H)-one 2

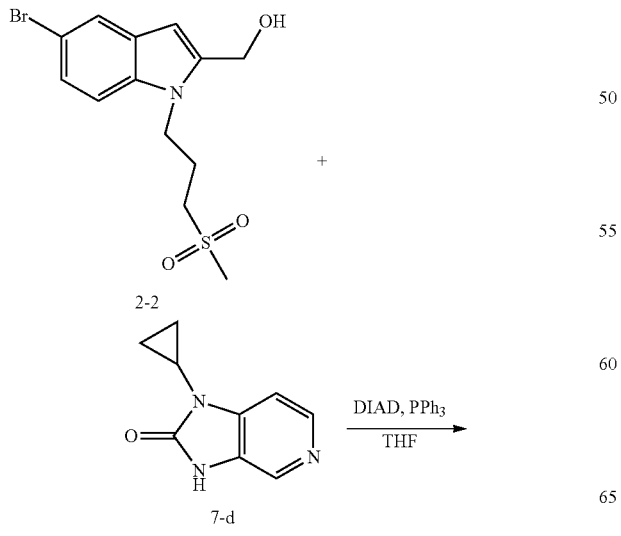

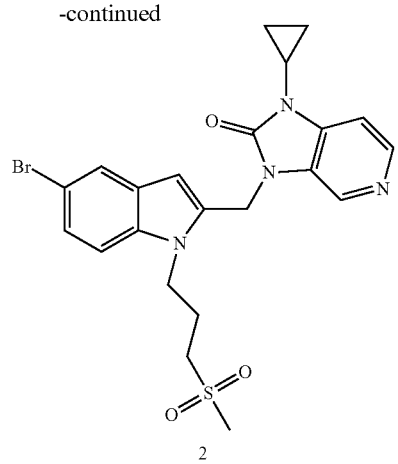

To a stirred solution of intermediate 2-2 (0.5 g, 1.3 mmol), triphenyl phosphine (0.37 g, 1.4 mmol) and the pyridobenzimidazolone 7-d (0.34 g, 2 mmol) in dry THF (30 mL) was added DIAD (94%, 0.71 mL, 1.36 mmol) drop wise at room temperature. The reaction mixture was stirred overnight. After the completion of reaction, the mixture was concentrated to dryness and the residue was purified by column chromatography eluted with ethyl acetate/CH$_2$Cl$_2$ then CH$_2$Cl$_2$/methanol to yield the title compound 2 (458 mg, 70%) as a white solid.

m/z=504 (M+H)$^+$. $^1$H NMR (400 MHz, CHLOROFORM-d) δ ppm 0.99-1.07 (m, 2 H), 1.13-1.21 (m, 2 H), 2.11 (m, 2 H), 2.86 (s, 3 H), 2.93-2.99 (m, 1 H), 3.00-3.07 (m, 2 H), 4.37-4.48 (m, 2 H), 5.22 (s, 2 H), 6.61 (s, 1 H), 7.12-7.21 (m, 2 H), 7.30 (dd, J=8.8, 1.8 Hz, 1 H), 7.71 (d, J=1.8 Hz, 1 H), 8.32 (d, J=5.3 Hz, 1 H), 8.40 (s, 1 H)

Example 3

Compound 1, 5, 6 and 8 were prepared in the same manner as compound 2.

3-((5-Chloro-1-(3-(methylsulfonyl)propyl)-1H-indol-2-yl)methyl)-1-cyclopropyl-1H-imidazo[4,5-c]pyridin-2(3H)-one 1

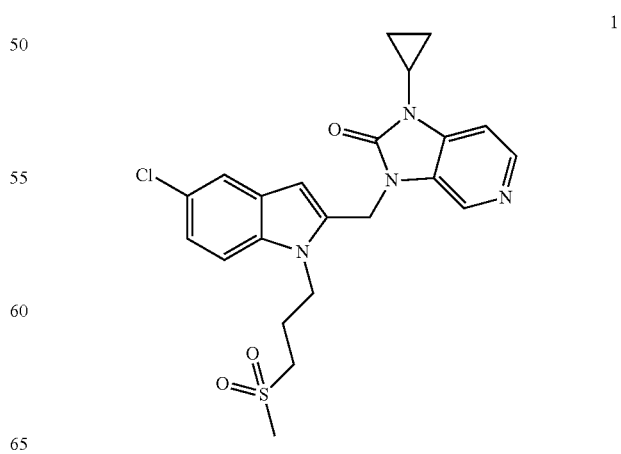

m/z=460 (M+H)$^+$.

¹H NMR (400 MHz, DMSO-d₆) δ ppm 0.90-0.97 (m, 2 H), 1.02-1.10 (m, 2 H), 1.86-1.99 (m, 2 H), 2.97 (s, 3 H), 2.98-3.03 (m, 1 H), 3.10-3.18 (m, 2 H), 4.38 (t, J=7.5 Hz, 2 H), 5.75 (s, 2 H), 6.53 (s, 1 H), 7.16 (dd, J=8.8, 2.0 Hz, 1 H), 7.27 (d, J=5.3 Hz, 1 H), 7.54 (d, J=8.8 Hz, 1 H), 7.57 (d, J=2.0 Hz, 1 H), 8.25 (d, J=5.3 Hz, 1 H), 8.40 (s, 1 H)

3-((5-Bromo-1-(3-(methylsulfonyl)propyl)-1H-indol-2-yl)methyl)-1-(oxetan-3-yl)-1H-imidazo[4,5-c]pyridin-2(3H)-one 5

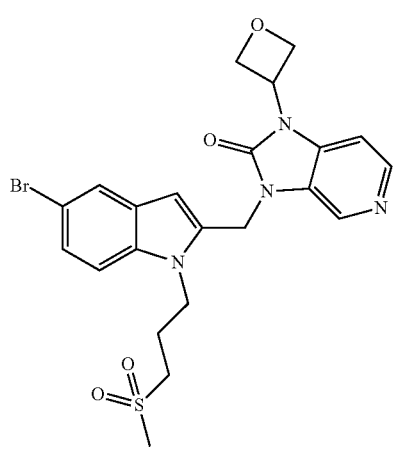

m/z=520 (M+H)⁺.

¹H NMR (400 MHz, DMSO-d₆) δ ppm 1.92 (ddd, J=15.2, 7.8, 7.7 Hz, 2 H), 2.96 (s, 3 H), 3.13 (m, 2 H), 4.38 (t, J=7.7 Hz, 2 H), 4.97 (d, J=7.8 Hz, 2 H), 5.07 (t, J=6.7 Hz, 2 H), 5.36 (s, 2 H), 5.56 (tdd, J=7.8, 7.8, 6.3, 6.1 Hz, 1 H), 6.56 (s, 1 H), 7.28 (dd, J=8.8, 2.0 Hz, 1 H), 7.50 (d, J=8.8 Hz, 1 H), 7.54 (d, J=5.3 Hz, 1 H), 7.71 (d, J=1.8 Hz, 1 H), 8.30 (d, J=5.5 Hz, 1 H), 8.41-8.57 (m, 1 H)

3-((5-Bromo-1-(3-(methylsulfonyl)propyl)-1H-indol-2-yl)methyl)-1-cyclopropyl-5-fluoro-1H-benzo[d]imidazol-2(3H)-one 6

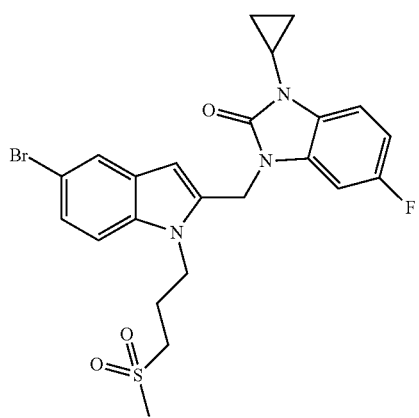

m/z=521 (M+H)⁺.

¹H NMR (400 MHz, CHLOROFORM-d) δ ppm 0.99-1.06 (m, 2 H), 1.09-1.17 (m, 2 H), 2.11 (m, 2 H), 2.85 (s, 3 H), 2.92 (m, 1 H), 2.97-3.05 (m, 2 H), 4.38-4.47 (m, 2 H), 5.16 (s, 2 H), 6.57 (s, 1 H), 6.76-6.84 (m, 1 H), 6.87 (dd, J=8.4, 2.0 Hz, 1 H), 7.12 (dd, J=8.4, 4.5 Hz, 1 H), 7.19 (d, J=8.8 Hz, 1 H), 7.30 (dd, J=8.8, 2.0 Hz, 1 H), 7.72 (d, J=1.8 Hz, 1 H)

3-((5-Chloro-1-(3-(methylsulfonyl)propyl)-1H-indol-2-yl)methyl)-1-cyclopropyl-5-fluoro-1H-benzo[d]imidazol-2(3H)-one 8

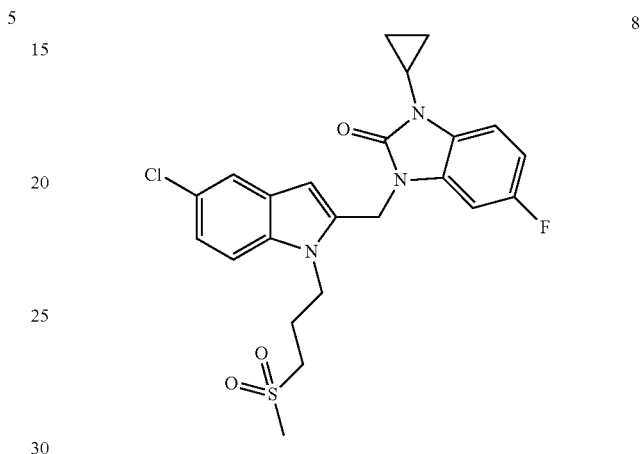

m/z=477 (M+H)⁺.

¹H NMR (400 MHz, CHLOROFORM-d) δ ppm 0.99-1.05 (m, 2 H), 1.10-1.17 (m, 2 H), 2.11-2.17 (m, 2 H), 2.85 (s, 3 H), 2.89-2.96 (m, 1 H), 2.97-3.05 (m, 2 H), 4.39-4.46 (m, 2 H), 5.16 (s, 2 H), 6.57 (s, 1 H), 6.77-6.84 (m, 1 H), 6.88 (dd, J=8.4, 2.4 Hz, 1 H), 7.12 (dd, J=8.7, 4.4 Hz, 1 H), 7.17 (m, J=2.0 Hz, 1 H), 7.21-7.25 (m, 1 H), 7.56 (d, J=1.5 Hz, 1 H)

Example 4

Synthesis of 3-((5-bromo-1-(4-(tert-butyldimethylsilyloxy)butyl)-1H-indol-2-yl)-methyl)-1-cyclopropyl-1H-imidazo[4,5-c]pyridin-2(3H)-one 11

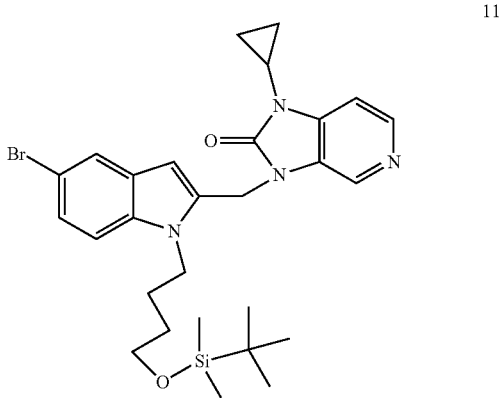 [SMILES: CC(C)(C)[Si](C)(C)OCCCCn1c(Cn2c(=O)n(C3CC3)c3ccncc32)cc2cc(Cl)ccc21]

Step 1: Synthesis of ethyl 5-bromo-1-(4-(tert-butyldimethylsilyloxy)butyl)-1H-indol-2-carboxylate 11-1

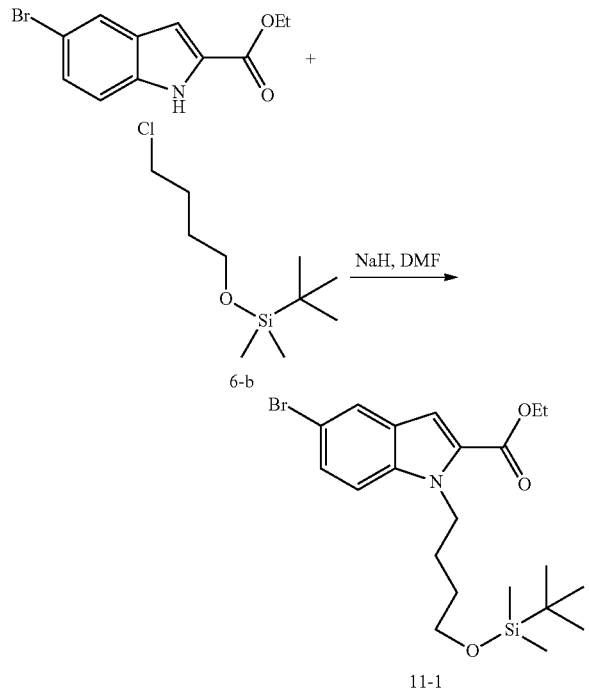

The ethyl 5-bromo-1H-indole-2-carboxylate which is commercially available (CAS 16732-70-0) (3 g, 11 mmol) was dissolved in DMF (50 mL) the mixture was stirred at room temperature then sodium hydride 60% suspension in mineral oil (0.49 g, 12.3-mmol) was added. The resulting mixture was stirred at room temperature for 1 hour. The tert-butyl(4-chlorobutoxy)dimethylsilane 6-b (2.5 g, 11.2 mmol) was added. The resulting mixture was stirred at 60° C. for 5 days. The mixture was allowed to cool down to room temperature then poured in iced watered solution then extracted with ethyl acetate. The organic layer was dried over MgSO$_4$ and concentrated to yield an orange oil. The crude was purified by column chromatography using dichloromethane/heptane to yield the title compound 11-1 (3.93 g, 77%) as a colorless oil. m/z=455 (M+H)$^+$.

Step 2: Synthesis of (5-bromo-1-(4-(tert-butyldimethylsilyloxy)butyl)-1H-indol-2-yl)-methanol 11-2

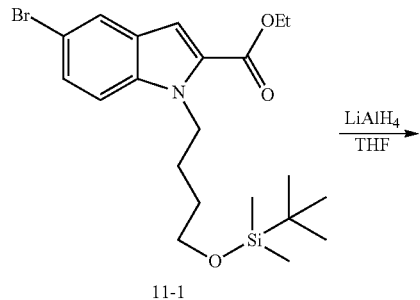

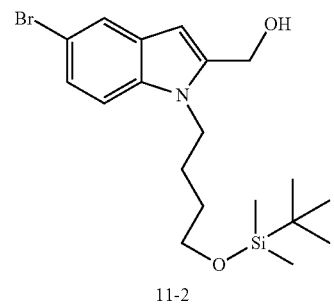

To a solution of intermediate 11-1 (3.93 g, 6.72 mmol) in THF (100 mL) was added at −78° C. lithium aluminum hydride 1 M solution in THF (8 mL, 8 mmol). The resulting mixture was stirred at room temperature for 4 hours. The reaction mixture was quenched by addition of ethyl acetate and ethanol. This mixture was poured in iced watered solution and the resulting mixture was filtered on celite. The aqueous layer was extracted with ethyl acetate (3×50 mL). The combined organic extracts were washed with brine (100 mL), dried over MgSO$_4$, filtered and concentrated under reduced pressure. The residue was purified by column chromatography using dichloromethane/methanol as the eluent. The intermediate 11-2 was collected as a colorless oil (2.68 g, 96%). m/z=413 (M+H)$^+$.

Step 3: Synthesis of 3-((5-bromo-1-(4-(tert-butyldimethylsilyloxy)butyl)-1H-indol-2-yl)methyl)-1-cyclopropyl-1H-imidazo[4,5-c]pyridin-2(3H)-one 11

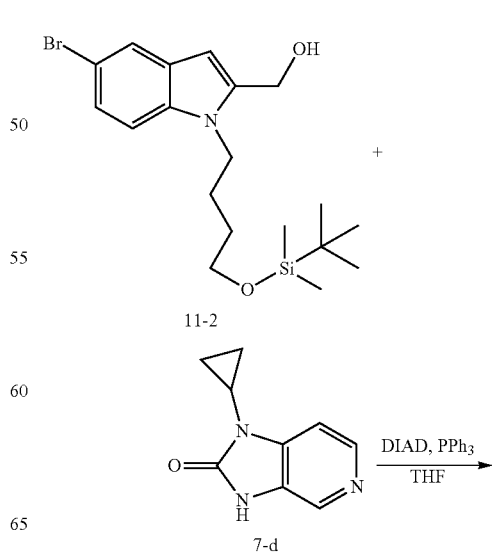

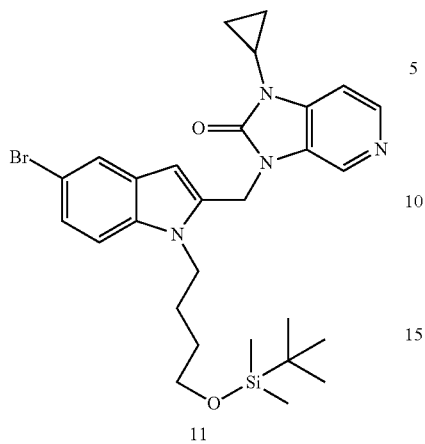

11

To a stirred solution of intermediate 11-2 (0.77 g, 1.86 mmol), triphenyl phosphine (0.54 g, 2.05 mmol) and the pyridobenzimidazolone 7-d (0.34 g, 2 mmol) in dry THF (30 mL) was added DIAD (94%, 0.38 mL, 1.96 mmol) drop wise at room temperature. The reaction mixture was stirred for night. After the completion of reaction, the mixture was concentrated to dryness the residue was purified by column chromatography eluted with ethyl acetate/CH$_2$Cl$_2$ then CH$_2$Cl$_2$/methanol to yield the title product 11 (1.06 g, 61%) as a colorless oil.

m/z=570 (M+H)$^+$. $^1$H NMR (400 MHz, DMSO-d$_6$) δ ppm-0.02 (s, 6 H), 0.79-0.83 (m, 9 H), 0.88-0.96 (m, 2 H), 1.03-1.12 (m, 2 H), 1.36-1.58 (m, 4 H), 2.93-3.03 (m, 1 H), 3.51 (t, J=6.1 Hz, 2 H), 4.24 (t, J=7.3 Hz, 2 H), 5.28 (s, 2 H), 6.56 (s, 1 H), 7.22 (dd, J=8.8, 2.0 Hz, 1 H), 7.27 (d, J=5.3 Hz, 1 H), 7.41 (d, J=8.8 Hz, 1 H), 7.70 (d, J=2.0 Hz, 1 H), 8.23 (d, J=5.3 Hz, 1 H), 8.34 (s, 1 H)

Example 5

Synthesis of 3-((5-chloro-1-(4-(tert-butyldimethylsilyloxy)butyl)-1H-indol-2-yl)ethyl)-1-cyclopropyl-1H-imidazo[4,5-c]pyridin-2(3H)-one 13

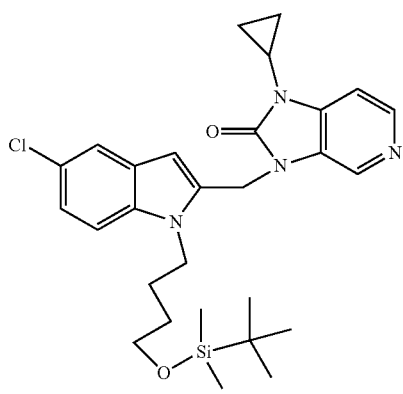

13

Compound 13 was prepared in the same manner as compound 11 starting from the commercially available indole. m/z=526 (M+H)$^+$.

Example 6

Synthesis of 3-((5-bromo-1-(4-hydroxybutyl)-1H-indol-2-yl)methyl)-1-cyclopropyl-1H-imidazo[4,5-c]pyridin-2(3H)-one 4

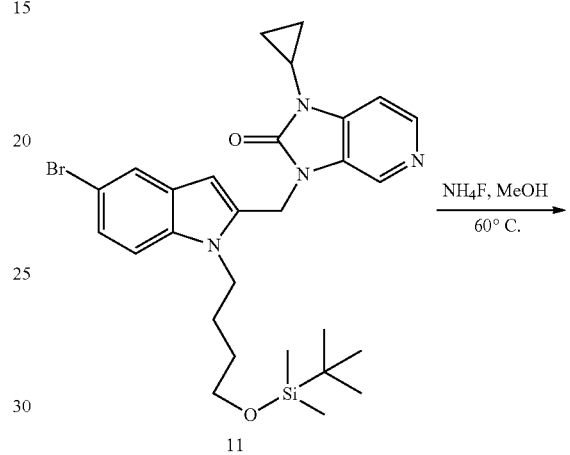

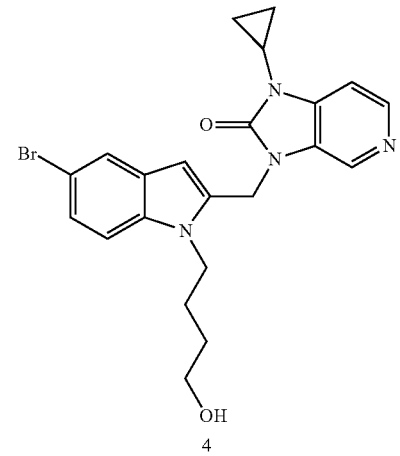

4

The intermediate 11 (1.06 g, 1.14 mmol) was dissolved in methanol (30 mL), and then ammonium fluoride (0.172 g, 4.6 mmol) was added. The resulting mixture was stirred at 60° C. overnight. The reaction mixture was allowed to cool down to room temperature, then the solvent was removed. The residue was purified by column chromatography dichloromethane methanol to yield the product as a white solid (323 mg, 62%). m/z=456 (M+H)$^+$.

$^1$H NMR (400 MHz, DMSO-d$_6$) δ ppm 0.88-0.97 (m, 2 H), 1.03-1.13 (m, 2 H), 1.32-1.53 (m, 4 H), 2.99 (dt, J=7.0, 3.4 Hz, 1 H), 3.34-3.40 (m, 2 H), 4.23 (t, J=7.4 Hz, 2 H), 4.40 (t, J=5.0 Hz, 1 H), 5.28 (s, 2 H), 6.55 (s, 1 H), 7.23 (dd, J=8.7, 1.9 Hz, 1 H), 7.27 (d, J=5.3 Hz, 1 H), 7.42 (d, J=8.8 Hz, 1 H), 7.70 (d, J=1.8 Hz, 1 H), 8.23 (d, J=5.3 Hz, 1 H), 8.34 (s, 1 H)

Example 7

Compounds 7, 9, 10, 15 and 16 were prepared in the same manner as compound 4 starting from the corresponding commercially available indoles.

3-((5-Chloro-1-(4-hydroxybutyl)-1H-indol-2-yl)methyl)-1-cyclopropyl-1H-imidazo[4,5-c]pyridin-2(3H)-one 7

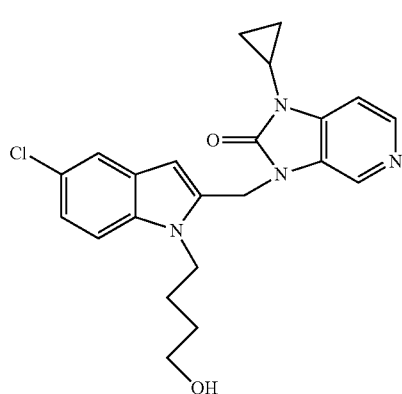

m/z=456 (M+H)$^+$.

$^1$H NMR (400 MHz, DMSO-d$_6$) δ ppm 0.87-0.97 (m, 2 H), 1.03-1.14 (m, 2 H), 1.31-1.57 (m, 4 H), 2.99 (m, 1 H), 3.26-3.43 (m, 2 H), 4.23 (t, J=7.3 Hz, 2 H), 4.40 (t, J=5.1 Hz, 1 H), 5.28 (s, 2 H), 6.55 (s, 1 H), 7.12 (dd, J=8.7, 2.1 Hz, 1 H), 7.27 (d, J=5.3 Hz, 1 H), 7.46 (d, J=8.8 Hz, 1 H), 7.55 (d, J=2.0 Hz, 1 H), 8.23 (d, J=5.0 Hz, 1 H), 8.35 (s, 1 H)

1-Cyclopropyl-3-((5-fluoro-1-(4-hydroxybutyl)-1H-indol-2-yl)methyl)-1H-imidazo[4,5-c]pyridin-2(3H)-one 9

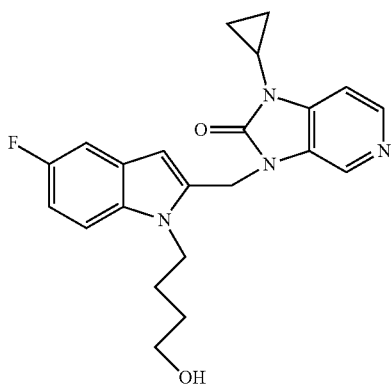

m/z=456 (M+H)$^+$.

$^1$H NMR (400 MHz, CHLOROFORM-d) δ ppm 0.97-1.06 (m, 2 H), 1.12-1.20 (m, 2 H), 1.54-1.74 (m, 4 H), 2.26 (br. s, 1 H), 2.89-3.00 (m, 1 H), 3.64 (t, J=5.9 Hz, 2 H), 4.17-4.29 (m, 2 H), 5.22 (s, 2 H), 6.60 (s, 1 H), 6.93 (td, J=9.2, 2.5 Hz, 1 H), 7.10-7.24 (m, 3 H), 8.29 (d, J=5.3 Hz, 1 H), 8.39 (s, 1 H)

1-Cyclopropyl-3-((1-(4-hydroxybutyl)-5-methoxy-1H-indol-2-yl)methyl)-1H-imidazo[4,5-c]pyridin-2(3H)-one 10

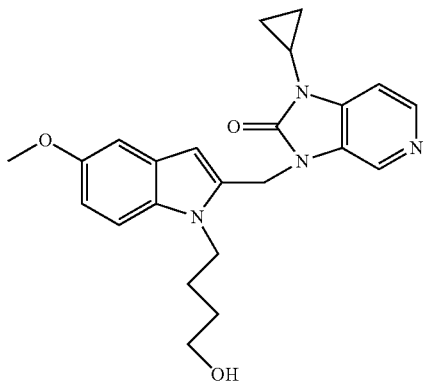

m/z=407 (M+H)$^+$.

$^1$H NMR (400 MHz, DMSO-d$_6$) δ ppm 0.87-0.96 (m, 2 H), 1.02-1.12 (m, 2 H), 1.30-1.50 (m, 4 H), 2.98 (dt, J=7.0, 3.5 Hz, 1 H), 3.27-3.29 (m, 2 H), 3.73 (s, 3 H), 4.17 (t, J=6.9 Hz, 2 H), 4.39 (t, J=5.0 Hz, 1 H), 5.24 (s, 2 H), 6.51 (s, 1 H), 6.76 (dd, J=8.8, 2.5 Hz, 1 H), 7.01 (d, J=2.5 Hz, 1 H), 7.26 (d, J=5.3 Hz, 1 H), 7.30 (d, J=8.8 Hz, 1 H), 8.22 (d, J=5.0 Hz, 1 H), 8.35 (s, 1 H)

3-((6-Chloro-1-(4-hydroxybutyl)-3-iodo-1H-indol-2-yl)methyl)-1-cyclopropyl-1H-imidazo[4,5-c]pyridin-2(3H)-one 15

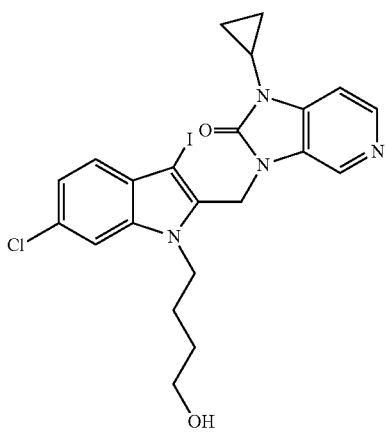

m/z=538 (M+H)$^+$.

$^1$H NMR (400 MHz, DMSO-d$_6$) δ ppm 0.88-0.97 (m, 2 H), 1.05-1.13 (m, 2 H), 1.16-1.27 (m, 2 H), 1.27-1.39 (m, 2 H), 2.99 (tt, J=7.0, 3.7 Hz, 1 H), 3.19-3.28 (m, 2 H), 4.14-4.28 (m, 2 H), 4.37 (t, J=4.9 Hz, 1 H), 5.30 (s, 2 H), 7.17 (dd, J=8.4, 1.9

Hz, 1 H), 7.27 (dd, J=5.1, 0.6 Hz, 1 H), 7.35 (d, J=8.5 Hz, 1 H), 7.64 (d, J=1.8 Hz, 1 H), 8.09 (s, 1 H), 8.22 (d, J=5.3 Hz, 1 H)

3-((6-Chloro-1-(4-hydroxybutyl)-1H-indol-2-yl) methyl)-1-cyclopropyl-1H-imidazo[4,5-c]pyridin-2 (3H)-one 16

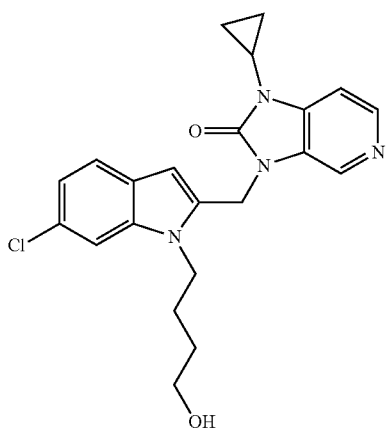

m/z=412 (M+H)+.

$^1$H NMR (400 MHz, DMSO-d$_6$) δ ppm 0.80-0.97 (m, 2 H), 1.00-1.19 (m, 2 H), 1.31-1.56 (m, 4 H), 2.87-3.10 (m, 1 H), 3.34-3.45 (m, 2 H), 4.22 (t, J=7.2 Hz, 2 H), 4.41 (t, J=5.0 Hz, 1 H), 5.27 (s, 2 H), 6.60 (s, 1 H), 7.01 (dd, J=8.3, 1.8 Hz, 1 H), 7.27 (dd, J=5.1, 0.6 Hz, 1 H), 7.51 (d, J=8.5 Hz, 1 H), 7.53-7.60 (m, 1 H), 8.23 (d, J=5.3 Hz, 1 H), 8.35 (s, 1 H)

Example 8

Synthesis of 5-((5-bromo-2-(1-cyclopropyl-2-oxo-1H-imidazo[4,5-c]pyridin-3 (2H)-yl)methyl)-1H-indol-1-yl)pentanenitrile 3

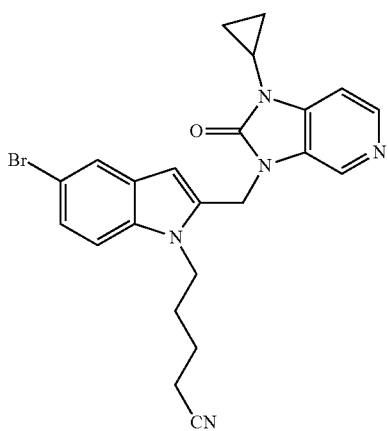

Step 1: Synthesis of 4-(5-bromo-2-((1-cyclopropyl-2-oxo-1H-imidazo[4,5-c]pyridin-3(2H)-yl)methyl)-1H-indol-1-yl)butyl 4-methylbenzensulfonate 3-1

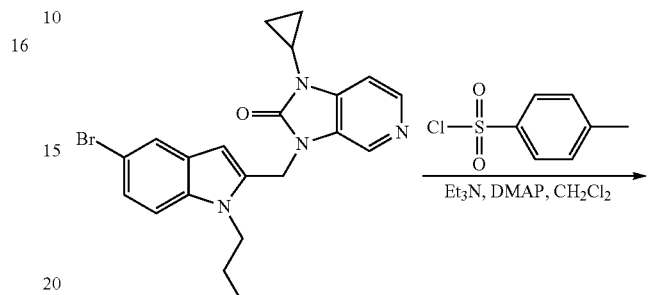

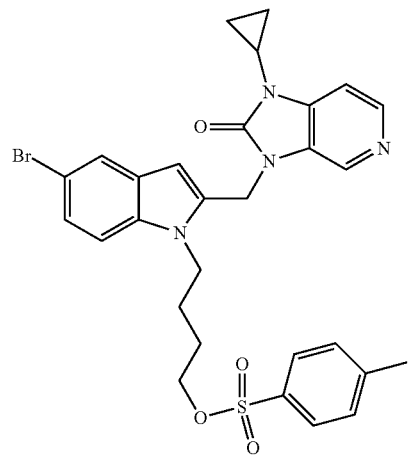

To a solution of compound 4 (0.88 g, 1.95 mmol) in dry dichloromethane (30 mL) under nitrogen were added triethylamine (0.81 mL, 5.83 mmol), 4-dimethyl amino pyridine (0.07 g, 0.58 mmol) and 4-methylbenzene-1-sulfonyl chloride (0.445 g, 2.33 mmol) at room temperature. The resulting mixture was stirred overnight under nitrogen. The reaction mixture was diluted with dichloromethane then washed with water, dried over MgSO$_4$ and concentrated. The residue was purified by column chromatography using dichloromethane and methanol. The intermediate 3-1 (760 mg, 65%) was isolated as a white foam.

m/z=610 (M+H)+.

Step 2: Synthesis of 5-((5-bromo-2-(1-cyclopropyl-2-oxo-1H-imidazo[4,5-c]pyridin-3(2H)-yl)methyl)-1H-indol-1-yl)pentanenitrile 3

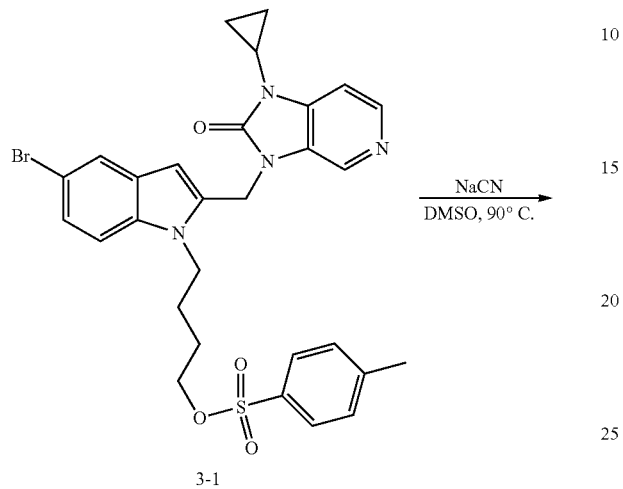

To the intermediate 3-1 (0.76 g, 1.25 mmol) in DMSO (30 mL), sodium cyanide (75 mg, 1.5 mmol) was added. The resulting mixture was stirred overnight under nitrogen at 90° C. The reaction mixture was allowed to cool down to room temperature then poured in to water/dichloromethane. The resulting mixture was extracted with dichloromethane, dried over MgSO$_4$ and concentrated. The obtained residue was purified by column chromatography eluting with dichloromethane/methanol to yield the title compound 3 (500 mg, 86%) as a white powder. m/z=465 (M+H)$^+$.

$^1$H NMR (400 MHz, CHLOROFORM-d) δ ppm 0.99-1.06 (m, 2 H), 1.15-1.21 (m, 2 H), 1.64-1.72 (m, 2 H), 1.72-1.82 (m, 2 H), 2.33 (t, J=6.8 Hz, 2 H), 2.95 (m, 1 H), 4.28 (t, J=7.2 Hz, 2 H), 5.21 (s, 2 H), 6.63 (s, 1 H), 7.10-7.16 (m, 2 H), 7.28 (dd, J=8.8, 1.8 Hz, 1 H), 7.71 (d, J=1.8 Hz, 1 H), 8.32 (d, J=5.3 Hz, 1 H), 8.39 (s, 1 H)

Example 9

Synthesis of 1-cyclopropyl-3-((1-isopentyl-1H-indol-2-yl)methyl)-1H-imidazo[4,5-c]pyridin-2(3H)-one 12

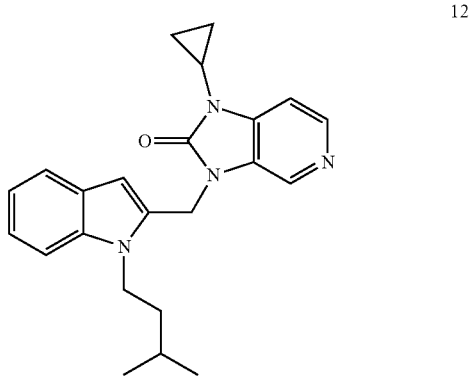 [SMILES: CC(C)CCn1c(Cn2c(=O)n(C3CC3)c3ccncc32)cc2ccccc21]

Step 1: Synthesis of (1-isopentyl-1H-indol-2yl)methanol 12-1

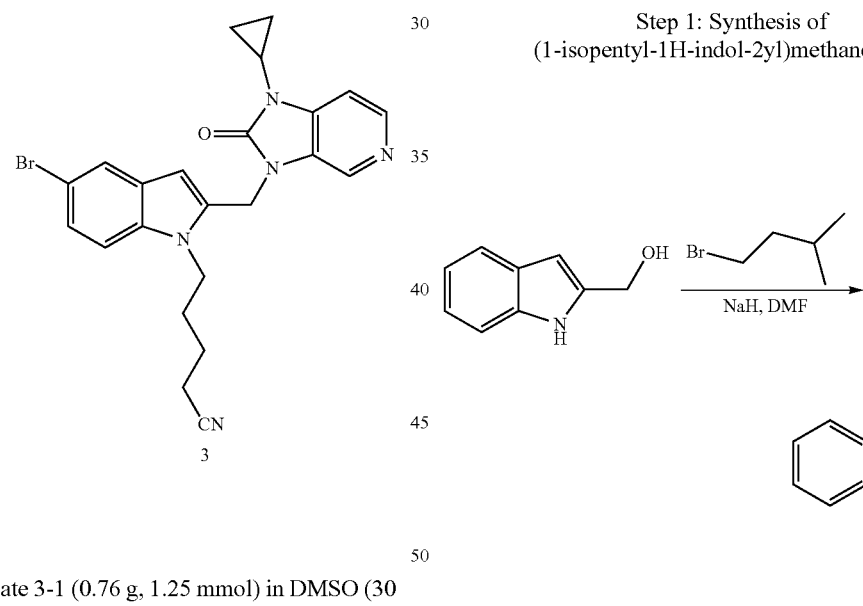

(1H-indole-2-yl)methanol (CAS 24621-70-3) (0.5 g, 3 mmol) was dissolved in DMF (20 mL) and the mixture was stirred at room temperature. Then sodium hydride 60% suspension in mineral oil (0.13 g, 3.43 mmol) was added. The resulting mixture was stirred at room temperature for 1 hour, then 1-bromo-3-methylbutane (CAS 107-82-4) (0.45 mL, 3.7 mmol) was added. The resulting mixture was stirred at room temperature overnight. The mixture was poured in ice/water solution and extracted with ethyl acetate. The organic layer was dried over MgSO$_4$ and concentrated to yield a black oil. The crude was purified by column chromatography using dichloromethane/ethyl acetate to yield the title compound 12-1 (177 mg, 26%) as a pink solid. m/z=218 (M+H)⁺.

Step 2: Synthesis of 1-cyclopropyl-3-((1-isopentyl-1H-indol-2-yl)methyl)-1H-imidazo4,5-c]pyridin-2(3H)-one 12

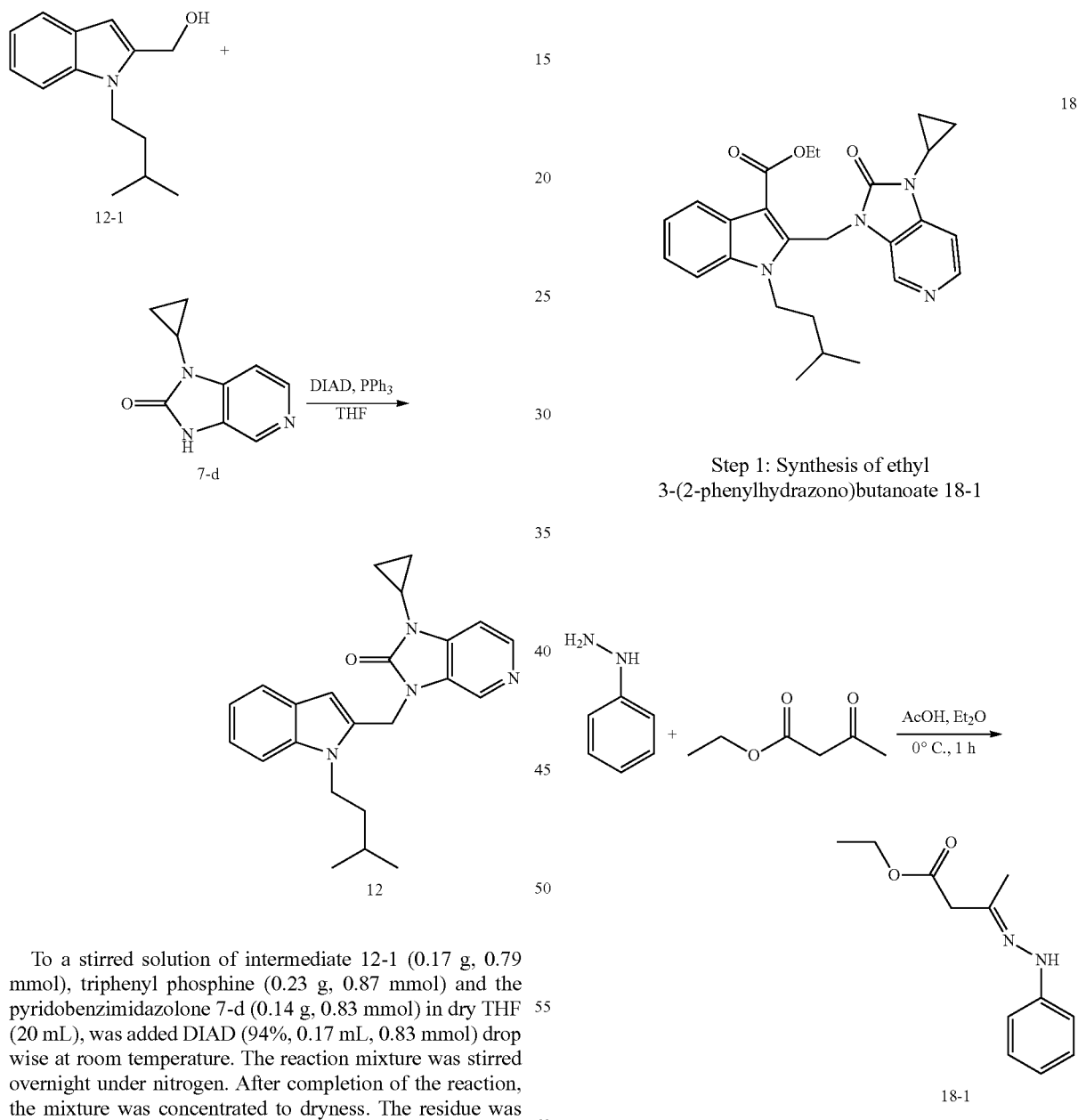

To a stirred solution of intermediate 12-1 (0.17 g, 0.79 mmol), triphenyl phosphine (0.23 g, 0.87 mmol) and the pyridobenzimidazolone 7-d (0.14 g, 0.83 mmol) in dry THF (20 mL), was added DIAD (94%, 0.17 mL, 0.83 mmol) drop wise at room temperature. The reaction mixture was stirred overnight under nitrogen. After completion of the reaction, the mixture was concentrated to dryness. The residue was purified by column chromatography eluted with ethyl acetate/ CH₂Cl₂ then CH₂Cl₂/methanol to yield the title compound 12 (68 mg, 22%) as a white powder. m/z=375 (M+H)⁺.

¹H NMR (400 MHz, DMSO-d₆) δ ppm 0.89 (d, J=6.6 Hz, 6 H), 0.90-0.95 (m, 2 H), 1.04-1.12 (m, 2 H), 1.20-1.30 (m, 2 H), 1.54-1.67 (m, 1 H), 2.98 (s, 1 H), 4.16-4.25 (m, 2 H), 5.28 (s, 2 H), 6.61 (s, 1 H), 7.01 (td, J=7.5, 0.9 Hz, 1 H), 7.13 (ddd, J=8.3, 7.1, 1.2 Hz, 1 H), 7.27 (dd, J=5.3, 0.8 Hz, 1 H), 7.35 (d, J=8.8 Hz, 0 H), 7.51 (d, J=7.8 Hz, 1 H), 8.22 (d, J=5.1 Hz, 1 H), 8.35 (s, 1 H)

Example 10

Synthesis of ethyl 2-((1-cyclopropyl-2-oxo-1H-imidazo[4,5-c]pyridin-3 (2H)-yl)ethyl)-1-isopentyl-1H-indole-3-carboxylate 18

Step 1: Synthesis of ethyl 3-(2-phenylhydrazono)butanoate 18-1

To a solution of phenyl hydrazine (125 g, 1150 mmol) and ethyl 3-oxobutanoate (100 g, 770 mmol) in terbutyl dimethyl ether (1000 mL) acetic acid (2 mL) was added. The resulting mixture was stirred at 0° C. for 1 h. The solvent was evaporated under vacuum. The residue (220 g) was used as such for next step.

Step 2: Synthesis of ethyl 2-methyl-1H-indole-3-carboxylate 18-2

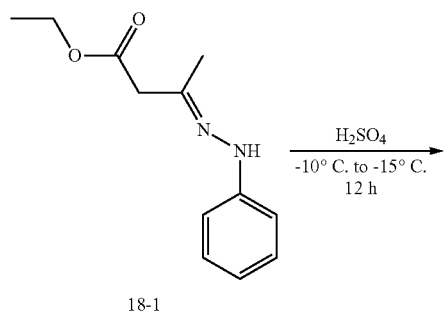

The intermediate 18-1 (160 g) was added to conc. H₂SO₄ (800 ml) portionwise at −10° C. under vigorous stirring. The solution was stirred for 1 h at −10° C. and for 2 h at 15° C. The solution was poured into ice-water and extracted with tert-butyl methyl ether. After the solvent was removed, the solid was washed with petroleum ether. The intermediate 18-2 was obtained (80 g, 70%)

Step 3: Synthesis of ethyl 1-isopentyl-2-methyl-1H-indole-3-carboxylate 18-3

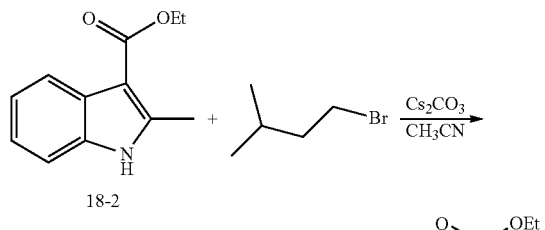

To a solution of intermediate 18-2 (38 g, 187 mmol) in CH₃CN (1000 mL) were added 1-bromo-3-methylbutane (94 ml, 747 mmol) and Cs₂CO₃ (121 g, 374 mmol). The resulting mixture was refluxed for 2 h. The solid was filtrated and the filtrate was evaporated under vacuum. The residue was purified by high-performance liquid chromatography (C18, eluent: CH₃OH/H₂O from 15/85 to 45/55 with 0.1% TFA as buffer). The pure fractions were collected and the volatiles were removed under vacuum and the aqueous solution was adjusted to pH=8 by addition of NaHCO₃. The residue was extracted with CH₂Cl₂ (2×100 mL). The organic layer was washed with brine (100 mL) and dried over Na₂SO₄. The solvent was removed under vacuum to yield the targeted intermediate 18-3 (20 g, 40%).

Step 4: Synthesis of ethyl 2-formyl-1-isopentyl-1H-indole-3-carboxylate 18-4

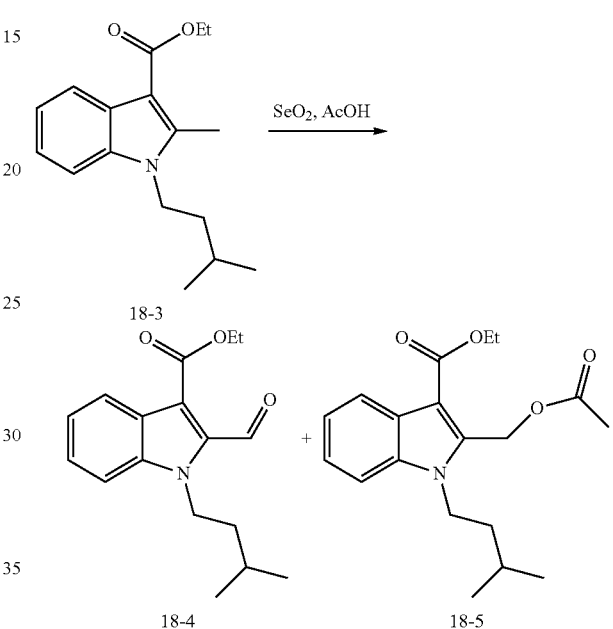

To a solution of intermediate 18-3 (9.8 g, 35.8 mmol) in acetic acid (150 mL) SeO₂ (14 g, 71.6 mmol) was added. The resulting mixture was refluxed for 12 h then allowed to cool down to room temperature. Then, water (200 mL) and CH₂Cl₂ (200 ml) were added. The organic layer was washed with brine (150 mL) and dried over Na₂SO₄. The solvent was removed under vacuum. The residue was used for the next step without further purification. The mixture of products was obtained (10 g, 70% of 18-5 and 10% of 18-4).

Step 5: Synthesis of ethyl 2-(hydroxymethyl)-1-isopentyl-1H-indole-3-carboxylate 18-6

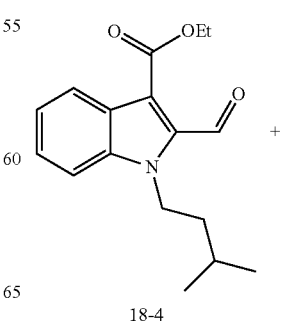

+

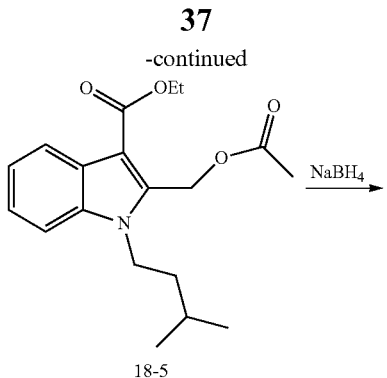

18-5

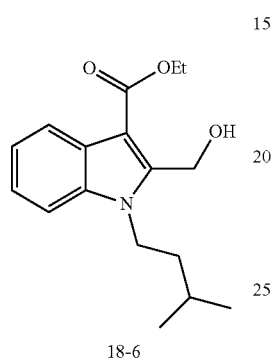

18-6

The mixture of intermediates 18-4 and 18-5 (10 g) was dissolved in methanol (100 mL) and cooled to −15° C. NaBH₄ (0.4 g, 10.4 mmol) was added portion wise. The mixture was stirred at −15° C. for 10 min and warmed to 15° C. for 0.5 h. Saturated NaHCO₃ was added. The solvent was removed under vacuum. CH₂Cl₂ (100 mL) and H₂O (100 mL) were added. The organic layer was washed with brine and dried over Na₂SO₄. The resulting residue was dissolved in methanol (150 mL). K₂CO₃ (9.8, 71.6 mmol) was added. The mixture was stirred at 15° C. for 2 h. The pH was adjusted to 4 by addition of 1 N HCl. The mixture was extracted with CH₂Cl₂ (200 mL). The organic layer was washed with brine and dried over Na₂SO₄. The solvent was removed under vacuum. The residue was purified by column (Eulent: petroleum ether/ethyl acetate=1:3) to yield intermediate 18-6 (3.63 g, 35% from 18-3) as white powder.

Step 6: Synthesis of ethyl 2-((1-cyclopropyl-2-oxo-1H-imidazo[4,5-c]pyridin-3(2H)-yl)methyl)-1-isopentyl-1H-indole-3-carboxylate 18

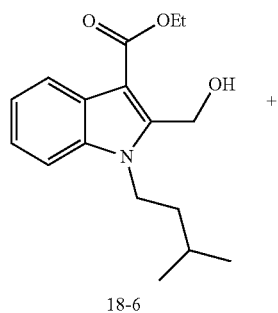

18-6

+

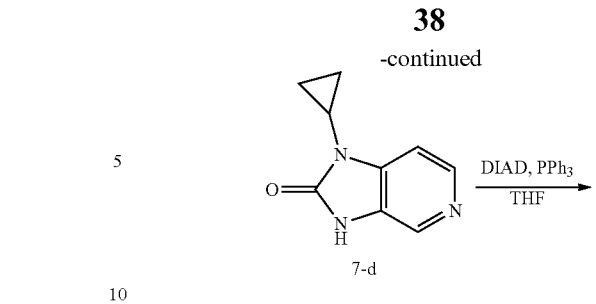

7-d

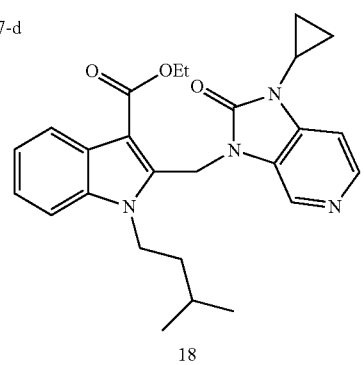

18

The same procedure as for the preparation of compound 12 was used for the synthesis of compound 18. m/z=447 (M+H)⁺.

¹H NMR (400 MHz, CHLOROFORM-d) δ ppm 0.89 (d, J=6.6 Hz, 6 H), 1.00-1.09 (m, 2 H), 1.10-1.24 (m, 4 H), 1.51 (t, J=7.1 Hz, 3 H), 1.57-1.73 (m, 1 H), 2.85-2.97 (m, 1 H), 4.16-4.29 (m, 2 H), 4.51 (q, J=7.3 Hz, 2 H), 5.88 (s, 2 H), 7.12 (d, J=5.1 Hz, 1 H), 7.21-7.32 (m, 3 H), 8.16-8.23 (m, 1 H), 8.27 (d, J=5.1 Hz, 1 H), 8.32 (s, 1 H)

Example 11

Synthesis of 2-((1-cyclopropyl-2-oxo-1H-imidazo[4,5-c]pyridin-3(2H)-yl)methyl)-1-isopentyl-1H-indole-3-carboxylic acid 17

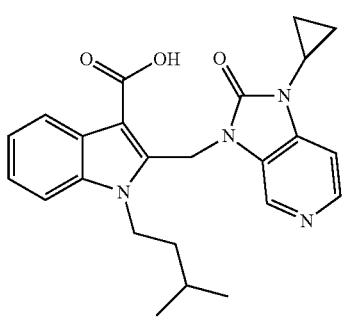

17

Compound 18 (0.5 g, 1 mmol) was dissolved in THF (25 mL), lithium hydroxide (48 mg, 2 mmol) dissolved in water (5 mL) was added. The resulting mixture was stirred at 60° C. overnight. The reaction mixture was allowed to cool down to room temperature then poured in water. The pH of the resulting mixture was adjusted to pH=4 by addition of a 1 M solution of hydrochloric acid. Then the mixture was extracted with ethyl acetate. The organic layer was dried over MgSO₄ and concentrated. The residue was purified by column chromatography using dichloromethane and methanol. The title compound 17 (400 mg, 94%) was isolated as a white powder. m/z=419 (M+H)⁺.

¹H NMR (360 MHz, DMSO-d₆) ppm 0.82 (d, J=6.6 Hz, 6 H), 0.88-0.95 (m, 2 H), 0.97-1.14 (m, 4 H), 1.49-1.64 (m, 1 H), 2.96 (m, 1 H), 4.21 (m, 2 H), 5.77 (s, 2 H), 7.19-7.31 (m, 3 H), 7.45 (d, J=7.7 Hz, 1 H), 8.08-8.14 (m, 1 H), 8.16 (s, 1 H), 8.21 (d, J=5.1 Hz, 1 H), 12.39-12.47 (m, 1 H)

Example 12

Synthesis of 2-((1-cyclopropyl-2-oxo-1H-imidazo[4,5-c]pyridin-3(2H)-yl)methyl)-1-isopentyl-1H-indole-3-carboxamide 14

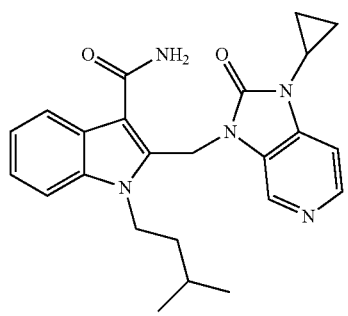

14

To compound 17 (150 mg, 0.36 mmol) in dry acetonitril (20 mL), carbonyl diimidazol (CDI) (145 mg, 0.9 mmol) was added. The resulting mixture was stirred at 50° C. under nitrogen overnight. After the formation of the intermediate, formed between the acid and CDI, the reaction mixture was allowed to cool down to room temperature. Then a solution of ammoniac in water (448 mg, 3.5 mmol) was added. The resulting mixture was stirred at room temperature for 2 hours. The precipitate was filtered off then washed successively with water and acetonitril. The resulting solid was dried in the oven to yield compound 14 (150 mg, 94%) as a white solid. m/z=418 (M+H)$^+$.

$^1$H NMR (360 MHz, CHLOROFORM-d) δ ppm 0.88 (d, J=6.6 Hz, 6 H), 0.99-1.07 (m, 2 H), 1.11-1.22 (m, 3 H), 1.55-1.71 (m, 4 H), 2.86-2.94 (m, 1 H), 4.16-4.25 (m, 2 H), 5.82 (s, 2 H), 7.12 (d, J=5.1 Hz, 1 H), 7.24-7.27 (m, 1 H), 7.28-7.34 (m, 2 H), 7.80-7.86 (m, 1 H), 8.28 (d, J=5.1 Hz, 1 H), 8.45 (s, 1 H)

Example 13

Synthesis of 2-((1-cyclopropyl-2-oxo-1H-imidazo[4,5-c]pyridin-3 (2H)-yl)methyl)-1-isopentyl-N-(methylsulfonyl)-1H-indole-3-carboxamide 19

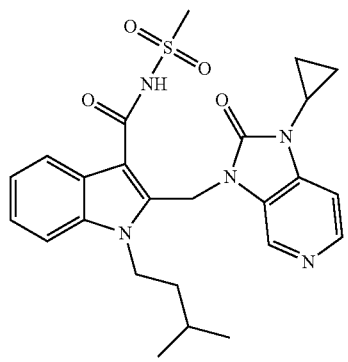

19

To compound 17 (200 mg, 0.47 mmol) in dry acetonitril (20 mL) carbonyl diimidazol (CDI) (170 mg, 1.05 mmol) was added. The resulting mixture was stirred at 50° C. under nitrogen overnight. After the formation of the intermediate, formed between the acid and CDI, the reaction mixture was allowed to cool down to room temperature. To the resulting mixture, methane sulfonamide (113.6 mg, 1.2 mmol) and DBU (0.18 mg, 1.2 mmol) were added. The resulting mixture was stirred at room temperature for 5 hours, then at 50° C. for 2 hours. The reaction mixture was allowed to cool down to room temperature. Then acetic acid (3 mmol) was added. The resulting mixture was concentrated, then the residue was dissolved in ethyl acetate and washed with water. The organic layer was dried over MgSO$_4$ and concentrated the residue was purified by column chromatography to yield compound 19 (120 mg, 50%) as a white solid. m/z=496 (M+H)$^+$.

$^1$H NMR (400 MHz, DMSO-d$_6$) δ ppm 0.80 (d, J=6.8 Hz, 6 H), 0.87-0.95 (m, 2 H), 1.00-1.17 (m, 4 H), 1.42-1.57 (m, 1 H), 2.93-3.01 (m, 1 H), 3.36 (s, 3 H), 4.14-4.26 (m, 2 H), 5.59 (s, 2 H), 7.22-7.30 (m, 2 H), 7.33 (d, J=5.5 Hz, 1 H), 7.47 (d, J=8.0 Hz, 1 H), 7.89 (d, J=7.5 Hz, 1 H), 8.26 (d, J=5.3 Hz, 1 H), 8.30 (s, 1 H)

Example 14

Synthesis of 5-chloro-2-((1-cyclopropyl-2-oxo-1H-imidazo[4,5-c]pyridin-3(2H)-yl)methyl)-1-(4-fluorobutyl)-1H-indole-3-carboxamide P54

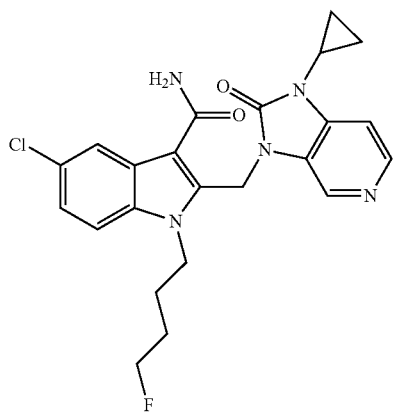

P54

Step 1: synthesis of methyl 5-chloro-1-(4-fluorobutyl)-2-(hydroxymethyl)-1H-indole-3-carboxylate 54-1

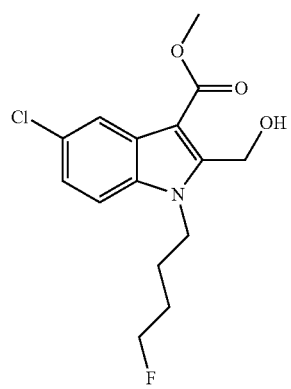

54-1

Methyl 5-chloro-1-(4-fluorobutyl)-2-(hydroxymethyl)-1H-indole-3-carboxylate 54-1 was synthesized following the procedure used for the synthesis of 18-6 (ie steps 3-5), starting from methyl 5-chloro-2-methyl-1H-indole-3-carboxylate (prepared as described in Angew. Chem. 2008, 47, 7230-7233) instead of 18-2, and 1-bromo-4-fluorobutane instead of 1-bromo-3-methylbutane.

Step 2

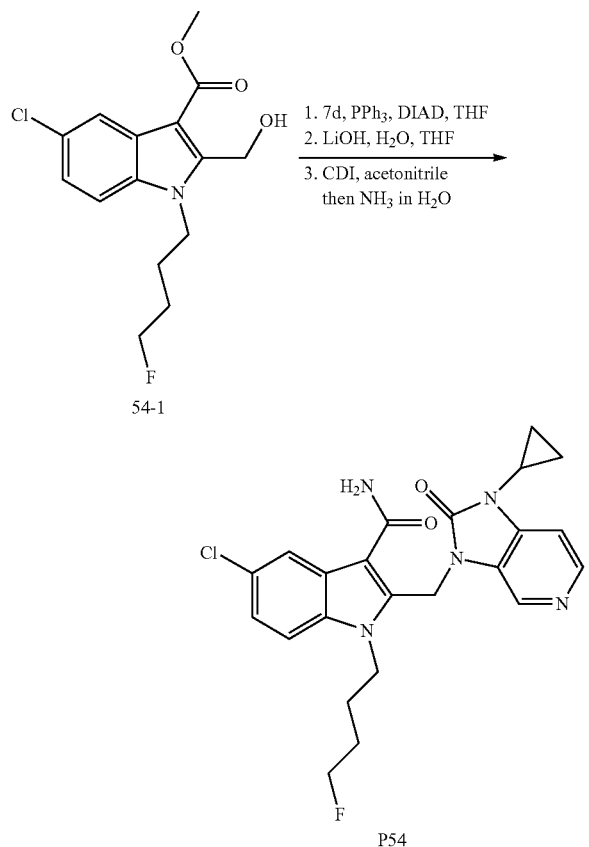 [SMILES: COC(=O)c1c(CO)n(CCCCF)c2ccc(Cl)cc12 ; "P54" ; NC(=O)c1c(Cn2c(=O)n(C3CC3)c3ccncc32)n(CCCCF)c2ccc(Cl)cc12]

The desired product P54 was synthesized following the steps reported for the synthesis of P14, starting from 54-1 instead of 18-6. m/z=456 (M+H)$^+$; $^1$H NMR (400 MHz, DMSO-d$_6$) δ ppm 0.82-0.94 (m, 2 H) 1.01-1.11 (m, 2 H) 1.20-1.33 (m, 2 H) 1.48-1.64 (m, 2 H) 2.92-3.01 (m, 1 H) 4.26 (s, 3 H) 4.39 (t, J=6.00 Hz, 1 H) 5.63 (s, 2 H) 7.23-7.28 (m, 2 H) 7.57 (d, J=8.78 Hz, 1 H) 7.86 (d, J=2.01 Hz, 1 H) 8.21 (d, J=5.27 Hz, 1 H) 8.39 (s, 1 H)

Example 15

Characterization of compounds 1-19 and P20-P81, and test for RSV inhibitory activity are shown in tables 1-3.

Example 16

Derivatives P82-P105 are prepared according to the methods described above and or in combination with methods as known in the art (Table 4).

General Experimental Details

HPLC-MS analysis was done using either one of the following methods:

Method 1:
The HPLC measurement was performed using an Agilent 1100 module comprising a pump, a diode-array detector (DAD) (wavelength used 220 nm), a column heater and a column as specified below. Flow from the column was split to an Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min. Reversed phase HPLC was carried out on a YMC-Pack ODS-AQ, 50×2.0 mm 5 mm column with a flow rate of 0.8 ml/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 ml were used. Oven temperature was 50° C. (MS polarity: positive)

Method 2:
The HPLC measurement was performed using an Agilent 1100 module comprising a pump, a diode-array detector (DAD) (wavelength used 220 nm), a column heater and a column as specified below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min. Reversed phase HPLC was carried out on a YMC-Pack ODS-AQ, 50×2.0 mm 5 mm column with a flow rate of 0.8 ml/min. Two mobile phases (mobile phase A: water with 0.1% TFA; mobile phase B: acetonitrile with 0.05% TFA) were used. First, 90% A and 10% B was hold for 0.8 minutes. Then a gradient was applied to 20% A and 80% B in 3.7 minutes and hold for 3 minutes. Typical injection volumes of 2 ml were used. Oven temperature was 50° C. (MS polarity: positive)

Method 3:
Column: XTerra MS C18 2.5μ, 4.6×50 mm, mobile phase A: 10 mM NH$_4$OOCH+0.1% HCOOH in H$_2$O, mobile phase B: MeOH operating at a column temperature of 50° C. using a flow rate of 1.5 mL/min. Gradient conditions: t=0 min: 65% A, 35% B; t =3.5 min, 5% A, 95% B; t=5.5 min, 5% A, 95% B; t=5.6 min: 65% A, 35% B; t=7 min, 65% A, 35% B.

Method 4:
Column: SunFire C18 3.5μ 4.6×100 mm, mobile phase A: 10 mM NH$_4$OOCH+0.1% HCOOH in H$_2$O, mobile phase B: MeOH operating at a column temperature of 50° C. using a flow rate of 1.5 mL/min. Gradient conditions: t=0 min: 65% A, 35% B; t=7 min, 5% A, 95% B; t=9.6 min, 5% A, 95% B; t=9.8 min: 65% A, 35% B; t=12 min, 65% A, 35% B.

NMR spectra were recorded on a Bruker Avance 400 spectrometer, operating at 400 MHz for $^1$H. Chemical shifts are given in ppm and a J value in Hz. Multiplicity is indicated using the following abbreviations: d for doublet, t for a triplet, m for a multiplet, etc. Thin-layer chromatography (TLC) was performed on 5×10 cm aluminium sheets coated with Silica-gel 60 F$_{254}$ (Merck KGaA).

Antiviral Activity

Black 96-well clear-bottom microtiter plates (Corning, Amsterdam, The Netherlands) were filled in duplicate using a customized robot system with serial 4-fold dilutions of compound in a final volume of 50 μl culture medium [RPMI medium without phenol red, 10% FBS, 0.04% gentamycin (50 mg/ml) and 0.5% DMSO]. Then, 100 μl of a HeLa cell suspension ($5 \times 10^4$ cells/ml) in culture medium was added to each well followed by the addition of 50 μl rgRSV224 (MOI=0.02) virus in culture medium using a multidrop dispenser (Thermo Scientific, Erembodegem, Belgium). rgRSV224 virus is an engineered virus that includes an additional GFP gene (Hallak et al, 2000) and was in-licensed from the NIH (Bethesda, Md., USA). Medium, virus- and mock-infected controls were included in each test. Cells were incubated at 37° C. in a 5% $CO_2$ atmosphere. Three days post-virus exposure, viral replication was quantified by measuring GFP expression in the cells by a MSM laser microscope (Tibotec, Beerse, Belgium). The $EC_{50}$ was defined as the 50% inhibitory concentration for GFP expression. In parallel, compounds were incubated for three days in a set of white 96-well microtiter plates (Corning) and the cytotoxicity of compounds in HeLa cells was determined by measuring the ATP content of the cells using the ATPlite kit (PerkinElmer, Zaventem, Belgium) according to the manufacturer's instructions. The $CC_{50}$ was defined as the 50% concentration for cytotoxicity.

REFERENCES

Hallak L K, Spillmann D, Collins P L, Peeples M E. Glycosaminoglycan sulfation requirements for respiratory syncytial virus infection. J. Virol. 740, 10508-10513 (2000).

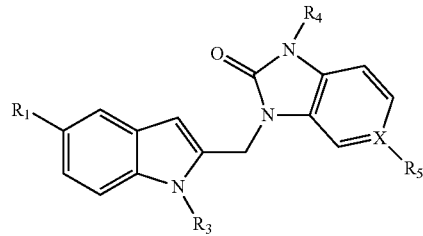

TABLE 1

| N° | $R_1$ | $R_3$ | $R_4$ | X—$R_5$ | WT activity $EC_{50}$ (μM) | Toxicity $CC_{50}$ (μM) |
|---|---|---|---|---|---|---|
| 1 | Cl | —(CH2)4—S(O)2—CH3 | cyclopropyl | N | 0.000286 | >9.83603 |
| 2 | Br | —(CH2)4—S(O)2—CH3 | cyclopropyl | N | 0.000288 | >9.83603 |
| 3 | Br | —(CH2)3—CN | cyclopropyl | N | 0.000452 | >9.83603 |
| 4 | Br | —(CH2)4—OH | cyclopropyl | N | 0.001117 | 48.65192 |
| 5 | Br | —(CH2)4—S(O)2—CH3 | oxetanyl | N | 0.001564 | >9.83603 |
| 6 | Br | —(CH2)4—S(O)2—CH3 | cyclopropyl | C—F | 0.001605 | >9.83603 |
| 7 | Cl | —(CH2)4—OH | cyclopropyl | N | 0.00224 | 47.59376 |
| 8 | Cl | —(CH2)4—S(O)2—CH3 | cyclopropyl | C—F | 0.003785 | >9.83603 |

TABLE 1-continued

| N° | R₁ | R₃ | R₄ | X—R₅ | WT activity EC₅₀ (μM) | Toxicity CC₅₀ (μM) |
|---|---|---|---|---|---|---|
| 9 | F | (CH₂)₅OH chain | cyclopropyl | N | 0.029368 | 50.28633 |
| 10 | OMe | (CH₂)₅OH chain | cyclopropyl | N | 0.038288 | >9.83603 |
| 12 | H | isopentyl | cyclopropyl | N | 0.360637 | 65.47266 |

Structure:

R₁-indole (with R₃ on N, R₂ at 3-position) linked via CH₂ to imidazo-pyridinone bearing R₄ on N, with X—R₅ on the pyridine ring.

TABLE 2

| N° | R₁ | R₂ | R₃ | R₄ | X—R₅ | WT activity EC₅₀ (μM) | Toxicity CC₅₀ (μM) |
|---|---|---|---|---|---|---|---|
| 14 | H | CONH₂ | isopentyl | cyclopropyl | N | 0.004507 | >24.5901 |
| 15 | Cl | I | (CH₂)₅OH | cyclopropyl | N | 0.076685 | >9.83603 |
| 16 | Cl | H | (CH₂)₅OH | cyclopropyl | N | 0.123894 | >9.83603 |
| 17 | H | CO₂H | isopentyl | cyclopropyl | N | 0.159012 | >98.3603 |

TABLE 2-continued
| N° | R₁ | R₂ | R₃ | R₄ | X—R₅ | WT activity EC$_{50}$ (μM) | Toxicity CC$_{50}$ (μM) |
|---|---|---|---|---|---|---|---|
| 18 | H | CO$_2$Et | isobutyl-CH$_2$- | cyclopropyl | N | 3.009193 | 32.11663 |
| 19 | H | CONHSO$_2$Me | isobutyl-CH$_2$- | cyclopropyl | N | 3.209445 | >9.83603 |
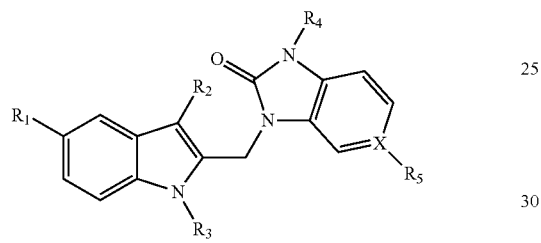

TABLE 3

| | $R_1$ | $R_2$ | $R_3$ | $R_4$ | $X-R_5$ | $^1H$ NMR | WT activity $EC_{50}$ (μM) | SI $CC_{50}/EC_{50}$ |
|---|---|---|---|---|---|---|---|---|
| P20 | F | H | (CH2)3-S(=O)2-CH3 | cyclopropyl | N | $^1$H NMR (400 MHz, DMSO-$d_6$) δ ppm 0.91-0.97 (m, 2 H) 1.03-1.11 (m, 2 H) 1.87-1.98 (m, 2 H) 2.93-3.04 (m, 4 H) 3.14 (t, J = 8.30 Hz, 2 H) 4.38 (t, J = 7.65 Hz, 2 H) 5.30 (s, 2 H) 6.52 (s, 1 H) 7.01 (td, J = 9.22, 2.63 Hz, 1 H) 7.24-7.31 (m, 2 H) 7.51 (dd, J = 9.03, 4.52 Hz, 1 H) 8.24 (d, J = 5.27 Hz, 1 H) 8.40 (s, 1 H) | 0.004066 | 15206 |
| P21 | Br | H | (CH2)3-S(=O)2-CH3 | cyclopropyl | C—H | $^1$H NMR (400 MHz, CHLOROFORM-d) δ ppm 0.98-1.06 (m, 2 H) 1.10-1.20 (m, 2 H) 2.11 (quin, J = 7.65 Hz, 2 H) 2.80 (s, 3 H) 2.89-3.06 (m, 3 H) 4.42 (t, J = 7.40 Hz, 2 H) 5.19 (s, 2 H) 6.58 (s, 1 H) 6.97-7.37 (m, 6 H) 7.70 (d, J = 1.25 Hz, 1 H) | 0.003877 | 6322 |
| P22 | F | H | (CH2)3-S(=O)2-CH3 | oxetanyl | N | $^1$H NMR (400 MHz, DMSO-$d_6$) δ ppm 1.86-1.99 (m, 2 H) 2.96 (s, 3 H) 3.14 (t, J = 8.00 Hz, 2 H) 4.38 (t, J = 7.65 Hz, 2 H) 4.96 (t, J = 7.50 Hz, 2 H) 5.07 (t, J = 6.53 Hz, 2 H) 5.35 (s, 2 H) 5.50-5.63 (m, 1 H) 6.56 (s, 1 H) 7.01 (td, J = 9.22, 2.38 Hz, 1 H) 7.28 (dd, J = 9.79, 2.51 Hz, 1 H) 7.48-7.60 (m, 2 H) 8.30 (d, J = 5.52 Hz, 1 H) 8.50 (s, 1 H) | 0.023809 | >4200 |
| P23 | CF$_3$ | H | (CH2)3-S(=O)2-CH3 | cyclopropyl | N | $^1$H NMR (400 MHz, CHLOROFORM-d) δ ppm 0.98-1.08 (m, 2 H) 1.14-1.22 (m, 2 H) 2.08-2.21 (m, 2 H) 2.90 (s, 3 H) 2.96-3.02 (m, 1 H) 3.07 (t, J = 7.53 Hz, 2 H) 4.49 (t, J = 7.80 Hz, 2 H) 5.27 (s, 2 H) 6.78 (s, 1 H) 7.18 (d, J = 5.02 Hz, 1 H) 7.40 (d, J = 8.78 Hz, 1 H) 7.47 (dd, J = 8.78, 1.51 Hz, 1 H) 7.90 (s, 1 H) 8.34 (br. s., 1 H) 8.42 (br. s., 1 H) | 0.007366 | 6557 |

TABLE 3-continued

| | R₁ | R₂ | R₃ | R₄ | X—R₅ | ¹H NMR | WT activity EC₅₀ (µM) | SI CC₅₀/EC₅₀ |
|---|---|---|---|---|---|---|---|---|
| P24 | H | H | (propyl methylsulfonyl) | (oxetanyl) | N | ¹H NMR (400 MHz, DMSO-d₆) δ ppm 1.91 (m, J = 15.31, 7.91, 7.91 Hz, 2 H) 2.96 (s, 3 H) 3.14 (t, J = 7.30 Hz, 2 H) 4.38 (t, J = 7.65 Hz, 2 H) 4.96 (t, J = 7.50 Hz, 2 H) 5.07 (t, J = 6.65 Hz, 2 H) 5.35 (s, 2 H) 5.52-5.64 (m, 1 H) 6.60 (s, 1 H) 6.98-7.07 (m, 1 H) 7.11-7.20 (m, 1 H) 7.46-7.59 (m, 3 H) 8.29 (d, J = 5.27 Hz, 1 H) 8.50 (s, 1 H) | 0.032617 | >3065 |
| P25 | H | H | (propyl methylsulfonyl) | (cyclopropyl) | N | ¹H NMR (400 MHz, DMSO-d₆) δ ppm 0.88-0.97 (m, 2 H) 1.03-1.12 (m, 2 H) 1.84-1.99 (m, 2 H) 2.96 (s, 3 H) 3.00 (dt, J = 6.96, 3.42 Hz, 1 H) 3.14 (t, J = 7.50 Hz, 2 H) 4.37 (t, J = 7.53 Hz, 2 H) 5.30 (s, 2 H) 6.56 (s, 1 H) 7.02 (t, J = 7.50 Hz, 1 H) 7.15 (t, J = 7.15 Hz, 1 H) 7.27 (d, J = 5.27 Hz, 1 H) 7.50 (t, J = 8.41 Hz, 2 H) 8.23 (d, J = 5.27 Hz, 1 H) 8.40 (s, 1H) | 0.009136 | >10945 |
| P26 | F | H | (propyl methylsulfonyl) | (cyclopropyl) | C—H | ¹H NMR (400 MHz, DMSO-d₆) δ ppm 0.89-0.96 (m, 2 H) 1.02-1.07 (m, 2 H) 1.92 (m, J = 7.53, 7.53 Hz, 2 H) 2.89-3.02 (m, 4 H) 3.14 (t, J = 7.50 Hz, 2 H) 4.39 (t, J = 7.53 Hz, 2 H) 5.24 (s, 2 H) 6.42 (s, 1 H) 6.95-7.12 (m, 3 H) 7.17-7.30 (m, 3 H) 7.50 (dd, J = 8.91, 4.39 Hz, 1 H) | 0.022641 | 2270 |
| P27 | F | H | (propyl methylsulfonyl) | (cyclopropyl) | C—F | ¹H NMR (400 MHz, DMSO-d₆) δ ppm 0.88-0.95 (m, 2 H) 1.01-1.06 (m, 2 H) 1.94 (quin, J = 7.72 Hz, 2 H) 2.87-3.04 (m, 4 H) 3.14 (t, J = 7.80 Hz, 2 H) 4.39 (t, J = 7.53 Hz, 2 H) 5.24 (s, 2 H) 6.44 (s, 1 H) 6.91 (quinquin, J = 8.78, 8.78, 8.78, 8.78, 2.51, 2.51, 2.51 Hz, 1 H) 7.00 (td, J = 9.16, 2.51 Hz, 1 H) 7.17 (dd, J = 9.16, 2.38 Hz, 1 H) 7.21 (dd, J = 8.53, 4.52 Hz, 1 H) 7.28 (dd, J = 9.79, 2.51 Hz, 1 H) 7.51 (dd, J = 8.91, 4.39 Hz, 1H) | 0.036014 | 664 |

TABLE 3-continued

| | $R_1$ | $R_2$ | $R_3$ | $R_4$ | $X-R_5$ | $^1$H NMR | WT activity $EC_{50}$ (μM) | SI $CC_{50}/EC_{50}$ |
|---|---|---|---|---|---|---|---|---|
| P28 | H | H | (butyl-methylsulfonyl group) | cyclopropyl | C—H | $^1$H NMR (400 MHz, DMSO-$d_6$) δ ppm 0.89-0.96 (m, 2 H) 1.01-1.07 (m, 2H) 1.91 (m, J = 15.25, 7.81 Hz, 2 H) 2.91-3.01 (m, 4 H) 3.08-3.20 (m, 2 H) 4.39 (t, J = 7.53 Hz, 2 H) 5.25 (s, 2 H) 6.47 (s, 1 H) 6.98-7.04 (m, 2 H) 7.07 (td, J = 7.50, 1.00 Hz, 1 H) 7.14 (m, J = 7.65, 7.65 Hz, 1 H) 7.23 (m, J = 7.00, 7.00 Hz, 2 H) 7.48 (dd, J = 7.78, 4.52 Hz, 2 H) | 0.348289 | 184 |
| P29 | F | H | (fluoroalkyl chain) | cyclopropyl | N | $^1$H NMR (400 MHz, DMSO-$d_6$) δ ppm 0.83-0.98 (m, 2 H) 1.01-1.14 (m, 2 H) 1.44-1.78 (m, 4 H) 2.92-3.04 (m, 1 H) 4.26 (t, J = 6.78 Hz, 2 H) 4.41 (dt, J = 47.18, 5.30 Hz, 2 H) 5.28 (s, 2 H) 6.56 (s, 1 H) 6.98 (t, J = 8.28 Hz, 1 H) 7.27 (m, J = 4.27 Hz, 2 H) 7.46 (dd, J = 8.66, 3.64 Hz, 1 H) 8.23 (d, J = 5.02 Hz, 1 H) 8.37 (s, 1 H) | 0.013779 | 2149 |
| P30 | Cl | H | (fluoroalkyl chain) | cyclopropyl | N | $^1$H NMR (400 MHz, CHLOROFORM-d) δ ppm 0.98-1.06 (m, 2 H) 1.11-1.22 (m, 2H), 1.58-1.81 (m, 4 H), 2.87-2.99 (m, 1 H), 4.24 (t, J = 7.4 Hz 2 H), 4.33 (t, J = 5.1 Hz, 1 H), 4.45 (t, J = 5.5 Hz, 1 H), 5.22 (s, 2 H), 6.59 (s, 1 H), 7.08-7.22 (m, 3 H), 7.54 (d, J = 1.5 Hz, 1 H), 8.30 (d, J = 5.3 Hz, 1H), 8.36 (s, 1 H) | 0.000733 | 24457 |
| P31 | Br | H | (trifluoroalkyl chain) | cyclopropyl | C—H | $^1$H NMR (400 MHz, DMSO-$d_6$) δ ppm 0.83-0.96 (m, 2 H), 1.02-1.13 (m, 2 H), 1.57-1.73 (m, 2 H), 2.17-2.35 (m, 2 H), 2.83-2.97 (m, 1H), 4.27-4.41 (m, 2 H), 5.25 (s, 2 H), 6.49 (s, 1 H), 6.96-7.12 (m, 2 H), 7.19 (d, J = 8.5 Hz, 1 H), 7.22-7.30 (m, 2 H), 7.48 (d, J = 8.8 Hz, 1 H), 7.70 (d, J = 1.8 Hz, 1 H) | 0.012131 | 3446 |
| P32 | Br | H | (trifluoroalkyl chain) | cyclopropyl | N | $^1$H NMR (400 MHz, DMSO-$d_6$) δ ppm 0.81-0.97 (m, 2 H), 1.01-1.13 (m, 2 H), 1.56-1.77 (m, 2 H), 2.16-2.39 (m, 2 H), 2.86-3.04 (m, 1H), 4.17-4.44 (m, 2 H), 5.30 (s, 2 H), 6.56 (s, 1 H), 7.18-7.35 (m, 2 H), 7.50 (d, J = 8.8 Hz, 1 H), 7.66-7.82 (m, 1 H), 8.25 (d, J = 5.3 Hz, 1H), 8.39 (s, 1 H) | 0.00034 | 53514 |

TABLE 3-continued

| | $R_1$ | $R_2$ | $R_3$ | $R_4$ | $X-R_5$ | $^1$H NMR | WT activity $EC_{50}$ (μM) | SI $CC_{50}/EC_{50}$ |
|---|---|---|---|---|---|---|---|---|
| P33 | Cl | H | -CH$_2$CH$_2$CH$_2$CN | cyclopropyl | N | $^1$H NMR (400 MHz, DMSO-d$_6$) δ ppm 0.90-0.97 (m, 2 H) 1.04-1.11 (m, 2 H) 1.88 (quin, J = 7.40 Hz, 2 H) 2.55 (t, J = 7.30 Hz, 2 H) 3.00 (tt, J = 6.90, 3.64 Hz, 1 H) 4.31 (t, J = 7.80 Hz, 2 H) 5.30 (s, 2 H) 6.45 (s, 1 H) 7.15 (dd, J = 8.78, 2.01 Hz, 1 H) 7.29 (d, J = 5.02 Hz, 1 H) 7.52 (d, J = 8.78 Hz, 1 H) 7.55 (d, J = 2.01 Hz, 1 H) 8.25 (d, J = 5.27 Hz, 1 H) 8.39 (s, 1 H) | 0.000266 | 190625 |
| P34 | F | H | -CH$_2$CH$_2$CH$_2$F | cyclopropyl | C—H | $^1$H NMR (400 MHz, DMSO-d$_6$) δ ppm 0.85-0.95 (m, 2 H) 1.02-1.13 (m, 2 H) 1.44-1.57 (m, 2 H) 1.57-1.74 (m, 2 H) 2.93 (tt, J = 6.68, 3.36 Hz, 1 H) 4.28 (t, J = 7.40 Hz, 2 H) 4.39 (dt, J = 47.43, 6.00 Hz, 2 H) 5.23 (s, 2 H) 6.47 (s, 1 H) 6.91-7.04 (m, 2 H) 7.04-7.12 (m, 1 H) 7.18 (d, J = 7.53 Hz, 1 H) 7.21-7.32 (m, 2 H) 7.44 (dd, J = 8.78, 4.27 Hz, 1 H) | 0.250865 | >398 |
| P35 | Cl | H | -CH$_2$CH$_2$CH$_2$CN | cyclopropyl | C—H | $^1$H NMR (400 MHz, DMSO-d$_6$) δ ppm 0.89-0.95 (m, 2 H) 1.03-1.10 (m, 2 H) 1.84 (quin, J = 7.53 Hz, 2 H) 2.54 (t, J = 7.50 Hz, 2 H) 2.95 (tt, J = 6.93, 3.48 Hz, 1 H) 4.31 (t, J = 7.80 Hz, 2 H) 5.25 (s, 2 H) 6.37 (s, 1 H) 7.03 (td, J = 7.50, 1.00 Hz, 0 H) 7.09 (td, J = 7.65, 1.00 Hz, 1 H) 7.13 (dd, J = 8.78, 2.01 Hz, 1 H) 7.19 (dd, J = 7.65, 0.63 Hz, 1 H) 7.26 (dd, J = 7.78, 0.75 Hz, 1 H) 7.50 (d, J = 8.78 Hz, 1 H) 7.53 (d, J = 2.01 Hz, 1 H) | 0.003138 | 5353 |
| P36 | Cl | H | -CH$_2$CH$_2$CH$_2$CF$_3$ | cyclopropyl | N | $^1$H NMR (400 MHz, CHLOROFORM-d) δ ppm 1.02 (m, J = 3.51, 1.51 Hz, 2 H), 1.18 (m, J = 5.77 Hz, 2 H), 1.77 (s, 2 H), 2.01-2.23 (m, 2 H), 2.91 (tdd, J = 6.96, 6.96, 3.64, 3.51 Hz, 1 H), 4.29 (t, J = 7.80 Hz, 2 H), 5.21 (s, 2 H), 6.66 (s, 1 H), 7.10-7.21 (m, 3 H), 7.56 (d, J = 0.75 Hz, 1 H), 8.32 (d, J = 5.27 Hz, 1 H), 8.40 (s, 1 H) | 0.000796 | 44701 |
| P37 | Cl | H | -CH$_2$CH$_2$CH$_2$CF$_3$ | cyclopropyl | C—F | $^1$H NMR (400 MHz, CHLOROFORM-d) δ ppm 0.97-1.05 (m, 2 H), 1.14 (dd, J = 6.9, 1.9 Hz, 2 H), 1.68-1.80 (m, 2 H), 2.02-2.18 (m, 2 H), 2.88-2.92 (m, 1 H), 4.25-4.36 (m, 2 H), 5.16 (s, 2 H), 6.61 (s, 1 H), 6.76-6.83 (m, 1 H), 6.87 (dd, J = 8.5, 2.5 Hz, 1 H), 7.10 (dd, J = 8.5, 4.5 Hz, 1 H), 7.14-7.21 (m, 2 H), 7.55-7.60 (m, 1 H) | 0.035934 | 1683 |

TABLE 3-continued

| | $R_1$ | $R_2$ | $R_3$ | $R_4$ | $X-R_5$ | $^1$H NMR | WT activity $EC_{50}$ (μM) | SI $CC_{50}/EC_{50}$ |
|---|---|---|---|---|---|---|---|---|
| P38 | Cl | H | CH₂CH₂CF₃ | cyclopropyl | C—H | $^1$H NMR (400 MHz, CHLOROFORM-d) δ ppm 0.98-1.06 (m, 2 H), 1.10-1.19 (m, 2 H), 1.69-1.82 (m, 2 H), 2.01-2.19 (m, 2 H), 2.89-2.92 (m, 1 H), 4.31 (t, J = 7.8 Hz, 2 H), 5.19 (s, 2 H), 6.61 (s, 1 H), 6.97-7.13 (m, 3 H), 7.15 (d, J = 1.0 Hz, 2 H), 7.21 (d, J = 7.8 Hz, 1 H), 7.55 (s, 1 H) | 0.05736 | 768 |
| P39 | Cl | H | CH₂CH₂CH₂F | cyclopropyl | C—F | $^1$H NMR (400 MHz, CHLOROFORM-d) δ ppm 0.98-1.05 (m, 2 H), 1.09-1.18 (m, 2 H), 1.60-1.77 (m, 4 H), 2.89-2.92 (m, 1 H), 4.25 (t, J = 7.5 Hz, 2 H), 4.31 (t, J = 5.3 Hz, 1 H), 4.43 (t, J = 5.6 Hz, 1 H), 5.17 (s, 2 H), 6.54 (s, 1 H), 6.78 (ddd, J = 9.7, 8.6, 2.5 Hz, 1 H), 6.83 (dd, J = 8.5, 2.3 Hz, 1 H), 7.09 (dd, J = 8.5, 4.3 Hz, 1 H), 7.12-7.16 (m, 1 H), 7.16-7.21 (m, 1 H), 7.55 (d, J = 1.8 Hz, 1 H) | 0.042078 | >1869 |
| P40 | Cl | H | CH₂CH₂CH₂CH₂S(O)₂CH₃ | cyclopropyl | C—H | $^1$H NMR (400 MHz, DMSO-d₆) δ ppm 0.88-0.96 (m, 2 H) 1.00-1.11 (m, 2 H) 1.93 (m, J = 7.28, 7.28 Hz, 2 H) 2.88-3.01 (m, 4 H) 3.08-3.19 (m, 2 H) 4.39 (t, J = 7.65 Hz, 2 H) 5.25 (s, 2 H) 6.42 (s, 1 H) 6.98-7.28 (m, 5 H) 7.49-7.57 (m, 2 H) | 0.002943 | >29923 |
| P41 | F | H | CH₂CH₂CH₂CH₂S(O)₂CH₃ | cyclopropyl | C—OCH₃ | $^1$H NMR (400 MHz, DMSO-d₆) δ ppm 0.86-0.93 (m, 2 H) 0.99-1.06 (m, 2 H) 1.86-1.98 (m, 2 H) 2.92 (dt, J = 6.90, 3.33 Hz, 1 H) 2.96 (s, 3 H) 3.09-3.17 (m, 2 H) 3.69 (s, 3 H) 4.38 (t, J = 7.65 Hz, 2 H) 5.22 (s, 2 H) 6.42 (s, 1 H) 6.67 (dd, J = 8.53, 2.26 Hz, 2 H) 6.85 (d, J = 2.26 Hz, 1 H) 6.99 (td, J = 9.29, 2.51 Hz, 1 H) 7.12 (d, J = 8.53 Hz, 1 H) 7.28 (dd, J = 9.79, 2.51 Hz, 1 H) 7.50 (dd, J = 9.03, 4.52 Hz, 1 H) | 0.063421 | 886 |
| P42 | Cl | H | CH₂CH₂CH₂F | cyclopropyl | C—H | $^1$H NMR (400 MHz, CHLOROFORM-d) δ ppm 0.99-1.06 (m, 2 H), 1.10-1.17 (m, 2 H), 1.58-1.68 (m, 3 H), 1.68-1.77 (m, 1 H), 2.9-2.95 (m, 1 H), 4.26 (t, J = 7.4 Hz, 2 H), 4.31 (t, J = 5.4 Hz, 1 H), 4.42 (t, J = 5.6 Hz, 1 H), 5.20 (s, 2 H), 6.54 (s, 1 H), 6.96-7.23 (m, 6 H), 7.53 (d, J = 1.8 Hz, 1 H) | 0.039716 | >2517 |

TABLE 3-continued

| | R₁ | R₂ | R₃ | R₄ | X—R₅ | ¹H NMR | WT activity EC₅₀ (µM) | SI CC₅₀/EC₅₀ |
|---|---|---|---|---|---|---|---|---|
| P43 | CN | H | CF₃-alkyl chain | cyclopropyl | N | ¹H NMR (400 MHz, CHLOROFORM-d) δ ppm 0.99-1.06 (m, 2 H) 1.15-1.23 (m, 2H) 1.75-1.85 (m, 2 H) 2.11-2.25 (m, 2 H) 2.88-2.96 (m, 1 H) 4.31-4.41 (m, 2 H) 5.25 (s, 2 H) 6.81 (s, 1 H) 7.18 (d, J = 5.27 Hz, 1 H) 7.32 (d, J = 8.78 Hz, 1H) 7.47 (dd, J = 8.66, 1.63 Hz, 1 H) 7.96 (d, J = 1.00 Hz, 1 H) 8.34 (d, J = 5.27 Hz, 1 H) 8.40 (s, 1 H) | 0.049625 | 1011 |
| P44 | Cl | H | CF₃-alkyl chain | cyclopropyl | C—CONHMe | ¹H NMR (400 MHz, CHLOROFORM-d) δ ppm 1.01-1.07 (m, 2 H) 1.13-1.20 (m, 2H) 1.64-1.80 (m, 4 H) 2.89-2.96 (m, 1 H) 2.99 (d, J = 4.77 Hz, 3 H) 4.29 (t, J = 7.40 Hz, 2 H) 4.32-4.37 (m, 1 H) 4.46 (t, J = 5.65 Hz, 1 H) 5.22 (s, 2 H) 6.00 (br. s., 1 H) 6.57 (s, 1 H) 7.12 (dd, J = 8.78, 2.01 Hz, 1 H) 7.19 (t, J = 9.50 Hz, 2 H) 7.45 (dd, J = 8.28, 1.51 Hz, 1 H) 7.52 (d, J = 1.76 Hz, 1 H) 7.58 (d, J = 1.51 Hz, 1 H) | 0.00198 | 9160 |
| P45 | Br | H | CF₃-alkyl chain | methylsulfonyl | N | ¹H NMR (400 MHz, DMSO-d₆) δ ppm 1.72-1.82 (m, 2 H) 2.25-2.39 (m, 2 H) 3.71 (s, 3 H) 4.30-4.37 (m, 2 H) 5.38 (s, 2 H) 6.60 (s, 1 H) 7.29 (dd, J = 8.78, 2.01 Hz, 1 H) 7.52 (d, J = 8.78 Hz, 1 H) 7.61 (d, J = 5.52 Hz, 1 H) 7.71 (d, J = 2.01 Hz, 1 H) 8.36 (d, J = 5.52 Hz, 1 H) 8.59 (d, J = 0.50 Hz, 1 H) | 0.000326 | 90696 |
| P46 | H | H | CF₃-alkyl chain | cyclopropyl | N | ¹H NMR (400 MHz, CHLOROFORM-d) δ ppm 0.96-1.06 (m, 2 H) 1.14-1.22 (m, 2 H) 1.73-1.84 (m, 2 H) 2.06-2.21 (m, 2 H) 2.88-2.97 (m, 1 H) 4.32 (t, J = 7.80 Hz, 2 H) 5.24 (s, 2 H) 6.73 (s, 1 H) 7.09-7.16 (m, 2 H) 7.19-7.26 (m, 2 H) 7.61 (d, J = 7.78 Hz, 1 H) 8.31 (d, J = 5.27 Hz, 1 H) 8.44 (s, 1 H) | 0.010295 | 6945 |
| P47 | H | H | F-alkyl chain | cyclopropyl | N | ¹H NMR (400 MHz, CHLOROFORM-d) δ ppm 0.96-1.07 (m, 2 H) 1.13-1.21 (m, 2H) 1.65-1.71 (m, 3 H) 1.72-1.80 (m, 1 H) 2.86-3.01 (m, 1 H) 4.28 (t, J = 7.40 Hz, 2 H) 4.34 (t, J = 5.27 Hz, 1 H) 4.45 (t, J = 5.65 Hz, 1 H) 5.25 (s, 2 H) 6.67 (s, 1 H) 7.11 (dd, J = 7.78, 0.75 Hz, 1 H) 7.14 (d, J = 5.27 Hz, 1 H) 7.21 (td, J = 7.65, 1.00 Hz, 1 H) 7.29 (d, J = 6.78 Hz, 1 H) 7.59 (d, J = 7.78 Hz, 1 H) 8.30 (d, J = 5.27 Hz, 1 H) 8.40 (s, 1H) | 0.01496 | 3489 |

TABLE 3-continued

| | $R_1$ | $R_2$ | $R_3$ | $R_4$ | $X-R_5$ | $^1$H NMR | WT activity $EC_{50}$ (μM) | SI $CC_{50}/EC_{50}$ |
|---|---|---|---|---|---|---|---|---|
| P48 | Cl | H | (chain with terminal CONH$_2$) | cyclopropyl | N | $^1$H NMR (400 MHz, DMSO-d$_6$) δ ppm 0.86-1.00 (m, 2 H) 1.04-1.13 (m, 2 H) 1.60-1.76 (m, 2 H) 2.25 (t, J = 7.40 Hz, 2 H) 2.91-3.05 (m, 1H) 4.16-4.34 (m, 2 H) 5.30 (s, 2 H) 6.52 (s, 1H) 7.15 (dd, J = 8.78, 2.01 Hz, 1 H) 7.28 (d, J = 5.02 Hz, 1 H) 7.51 (d, J = 8.78 Hz, 1 H) 7.57 (d, J = 2.01 Hz, 1 H) 8.25 (d, J = 5.27 Hz, 1 H) 8.38 (s, 1 H) | 0.045859 | >2180 |
| P49 | Cl | H | (chain with terminal CONHOH) | cyclopropyl | N | $^1$H NMR (400 MHz, DMSO-d$_6$) δ ppm 0.89-0.99 (m, 2 H) 1.03-1.12 (m, 2H) 1.58-1.75 (m, 2H) 2.03 (t, J = 7.28 Hz, 2 H) 3.01 (tt, J = 6.93, 3.61, 1 H) 4.10-4.33 (m, 2 H) 5.30 (s, 2 H) 6.50 (s, 1 H) 7.14 (dd, J = 8.78, 2.01 Hz, 1 H) 7.29 (d, J = 5.27 Hz, 1 H) 7.50 (d, J = 8.78 Hz, 1 H) 7.56 (d, J = 2.01 Hz, 1 H) 8.25 (d, J = 5.27 Hz, 1 H) 8.37 (s, 1 H) 8.73 (br. s., 1 H) 10.21 (br. s, 1 H) | 0.011416 | 1657 |
| P50 | Cl | H | (chain with terminal SO$_2$Me) | CF$_3$CH$_2$- | C—F | $^1$H NMR (400 MHz, CHLOROFORM-d) δ ppm 1.99-2.11 (m, 2 H) 2.88 (s, 3 H) 3.03 (t, J = 7.53 Hz, 2 H) 4.36-4.44 (m, 2 H) 4.51 (q, J = 8.50 Hz, 2 H) 5.25 (s, 2 H) 6.62 (s, 1 H) 6.82-6.89 (m, 1 H) 6.96 (dd, J = 8.28, 2.26 Hz, 1 H) 7.01 (dd, J = 8.53, 4.27 Hz, 1 H) 7.20 (dd, J = 8.78, 2.01 Hz, 1 H) 7.24 (d, J = 8.78 Hz, 1 H) 7.59 (d, J = 1.51 Hz, 1 H) | 0.004804 | 5176 |
| P51 | Cl | H | (chain with terminal C(=NH)NHOH) | cyclopropyl | N | $^1$H NMR (400 MHz, CHLOROFORM-d) δ ppm 1.13-1.25 (m, 2 H) 1.28-1.39 (m, 2 H) 1.84-2.00 (m, 2 H) 2.27 (t, J = 7.00 Hz, 2 H) 3.16-3.32 (m, 1 H) 4.39-4.57 (m, 2 H) 5.54 (s, 2 H) 6.74 (s, 1 H) 7.39 (dd, J = 8.78, 2.01 Hz, 1 H) 7.53 (d, J = 5.27 Hz, 1 H) 7.75 (d, J = 8.78 Hz, 1 H) 7.80 (d, J = 2.01 Hz, 1 H) 8.49 (d, J = 5.27 Hz, 1 H) 8.62 (s, 1 H) | 0.002627 | 5942 |
| P52 | Cl | H | (chain with terminal CH$_2$F) | CF$_3$CH$_2$- | N | $^1$H NMR (400 MHz, DMSO-d$_6$) δ ppm 1.52-1.71 (m, 4 H) 4.27 (t, J = 7.28 Hz, 2 H) 4.33 (t, J = 5.50 Hz, 1 H) 4.45 (t, J = 5.90 Hz, 1 H) 4.90 (q, J = 9.29 Hz, 2 H) 5.38 (s, 2 H) 6.55 (s, 1 H) 7.14 (dd, J = 8.66, 2.13 Hz, 1 H) 7.43 (d, J = 5.27 Hz, 1 H) 7.50 (d, J = 8.78 Hz, 1 H) 7.57 (d, J = 2.01 Hz, 1 H) 8.30 (d, J = 5.27 Hz, 1 H) 8.46 (s, 1 H) | 0.003139 | 20952 |

TABLE 3-continued

| | $R_1$ | $R_2$ | $R_3$ | $R_4$ | X—$R_5$ | $^1$H NMR | WT activity $EC_{50}$ (μM) | SI $CC_{50}/EC_{50}$ |
|---|---|---|---|---|---|---|---|---|
| P53 | Cl | COOH | [fluoroalkyl chain] | [cyclopropyl] | N | $^1$H NMR (400 MHz, DMSO-$d_6$) δ ppm 0.86-0.96 (m, 2 H) 1.03-1.11 (m, 2 H) 1.25-1.37 (m, 2 H) 1.50-1.67 (m, 2 H) 2.88-3.00 (m, 1 H) 4.22-4.33 (m, 3 H) 4.40 (t, J = 5.90 Hz, 1 H) 5.75 (br. s, 2 H) 7.26 (d, J = 5.27 Hz, 1 H) 7.30 (dd, J = 8.78, 2.01 Hz, 1 H) 7.62 (d, J = 8.78 Hz, 1 H) 8.08 (d, J = 2.01 Hz, 1 H) 8.18 (s, 1 H) 8.21 (d, J = 5.27 Hz, 1 H) | 0.024737 | >4042 |
| P54 | Cl | CONH$_2$ | [fluoroalkyl chain] | [cyclopropyl] | N | $^1$H NMR (400 MHz, DMSO-$d_6$) δ ppm 0.82-0.94 (m, 2 H) 1.01-1.11 (m, 2 H) 1.20-1.33 (m, 2 H) 1.48-1.64 (m, 2 H) 2.92-3.01 (m, 1 H) 4.26 (s, 3 H) 4.39 (t, J = 6.00 Hz, 1 H) 5.63 (s, 2 H) 7.23-7.28 (m, 2 H) 7.57 (d, J = 8.78 Hz, 1 H) 7.86 (d, J = 2.01 Hz, 1 H) 8.21 (d, J = 5.27 Hz, 1 H) 8.39 (s, 1 H) | 0.0000528 | >603587 |
| P55 | Cl | H | [trifluoromethyl-alkyl-sulfonylmethyl chain] | [CF$_3$-gem-difluoroalkyl] | N | $^1$H NMR (400 MHz, DMSO-$d_6$) δ ppm 1.88-2.02 (m, 2 H) 2.97 (s, 3 H) 3.15 (t, J = 8.00 Hz, 2 H) 4.38 (t, J = 7.50 Hz, 2 H) 4.89 (q, J = 9.00 Hz, 2 H) 5.40 (s, 2 H) 6.48 (s, 1 H) 7.17 (dd, J = 8.78, 2.01 Hz, 1 H) 7.44 (d, J = 5.27 Hz, 1 H) 7.54 (d, J = 8.78 Hz, 1 H) 7.57 (d, J = 2.01 Hz, 1 H) 8.31 (d, J = 5.27 Hz, 1 H) 8.49 (s, 1 H) | <0.000157 | >258982 |
| P57 | Cl | H | [trifluoromethyl-alkyl chain] | [CF$_3$-gem-difluoroalkyl] | N | $^1$H NMR (400 MHz, DMSO-$d_6$) δ ppm 1.64-1.80 (m, 2 H) 2.18-2.37 (m, 2 H) 4.33 (t, J = 7.65 Hz, 2 H) 4.90 (q, J = 9.29 Hz, 2 H) 5.40 (s, 2 H) 6.54 (s, 1 H) 7.17 (dd, J = 8.78, 2.01 Hz, 1 H) 7.44 (d, J = 5.27 Hz, 1 H) 7.55 (d, J = 8.78 Hz, 1 H) 7.58 (d, J = 1.76 Hz, 1 H) 8.31 (d, J = 2.01 Hz, 1 H) 8.49 (s, 1 H) | 0.000641 | 93005 |
| P58 | Cl | H | [morpholinoalkyl chain] | [cyclopropyl] | N | $^1$H NMR (360 MHz, DMSO-$d_6$) δ ppm 0.86-1.00 (m, 2 H) 1.03-1.13 (m, 2 H), 1.70 (quin, J = 6.6 Hz, 2 H), 2.12 (t, J = 6.6 Hz, 2 H), 2.19-2.31 (m, 4 H), 2.99 (m, J = 6.8, 3.2, 3.2 Hz, 1 H), 3.57 (br. s., 4 H), 4.28 (t, J = 6.6 Hz, 2 H), 5.35 (s, 2 H), 6.51 (s, 1 H), 7.12 (dd, J = 8.6, 1.6 Hz, 1 H), 7.28 (d, J = 5.1 Hz, 1 H), 7.49 (d, J = 8.8 Hz, 1 H), 7.55 (d, J = 1.5 Hz, 1 H), 8.24 (d, J = 5.1 Hz, 1 H), 8.36 (s, 1 H) | 0.005796 | 7416 |

TABLE 3-continued

| | R₁ | R₂ | R₃ | R₄ | X—R₅ | ¹H NMR | WT activity EC₅₀ (μM) | SI CC₅₀/EC₅₀ |
|---|---|---|---|---|---|---|---|---|
| P59 | Cl | COOH | CH₂CH₂C(F)(F)(F) | cyclopropyl | N | ¹H NMR (400 MHz, DMSO-d₆) δ ppm 0.90 (br. s., 2 H), 1.09 (d, J = 5.8 Hz, 2 H), 1.46 (br. s., 2 H), 2.25 (dd, J = 16.6, 10.8 Hz, 2 H), 2.93 (br. s., 1 H), 4.32 (t, J = 7.4 Hz, 2 H), 5.81 (s, 2 H), 7.19-7.37 (m, 2 H), 7.64 (d, J = 8.5 Hz, 1 H), 8.17 (s, 1 H), 8.20-8.26 (m, 1 H), 8.31 (s, 1 H) | 0.007162 | >13962 |
| P60 | Cl | COOH | CH₂CH₂CH₂F | cyclopropyl | C—F | ¹H NMR (400 MHz, DMSO-d₆) δ ppm 0.86-0.96 (m, 2 H), 1.02-1.13 (m, 2 H), 1.22-1.39 (m, 2 H), 1.48-1.74 (m, 2 H), 2.91-3.0 (m, 1 H), 4.21-4.35 (m, 3 H), 4.40 (t, J = 5.9 Hz, 1 H), 5.71 (s, 2 H), 6.84-6.94 (m, 1 H), 6.98 (dd, J = 9.3, 2.3 Hz, 1 H), 7.20 (dd, J = 8.5, 4.8 Hz, 1 H), 7.29 (dd, J = 8.8, 2.0 Hz, 1 H), 7.61 (d, J = 8.8 Hz, 1 H), 8.08 (d, J = 1.5 Hz, 1 H), 12.51-13.63 (m, 1 H) | 0.154159 | 277 |
| P61 | Cl | CONH₂ | CH₂CH₂C(F)(F)(F) | cyclopropyl | N | ¹H NMR (400 MHz, DMSO-d₆) δ ppm 0.86-0.93 (m, 2 H), 1.04-1.13 (m, 2 H), 1.40 (br. s., 2 H), 2.18-2.22 (m, 2 H), 2.87-2.98 (m, 1 H), 4.28 (t, J = 7.9 Hz, 2 H), 5.63 (s, 2 H), 7.21-7.34 (m, 2 H), 7.5-7.75 (m, 2H), 7.63 (d, J = 8.8 Hz, 1 H), 7.86 (d, J = 1.8 Hz, 1 H), 8.22 (d, J = 5.3 Hz, 1 H), 8.40 (s, 1 H) | <0.000153 | >245019 |
| P62 | Cl | H | CH₂CH₂CN | CH₂C(F)(F)(F) | N | ¹H NMR (400 MHz, CHLOROFORM-d) δ ppm 1.86-2.04 (m, 2 H) 2.39 (t, J = 7.03 Hz, 2 H) 4.35 (t, J = 7.80 Hz, 2 H) 4.53 (q, J = 8.50 Hz, 2 H) 5.30 (s, 2 H) 6.68 (s, 1 H) 7.06 (d, J = 5.27 Hz, 1 H) 7.21 (dd, J = 8.78, 2.01 Hz, 1 H) 7.25 (d, J = 8.78 Hz, 1 H) 7.58 (d, J = 1.76 Hz, 1 H) 8.40 (d, J = 5.27 Hz, 1 H) 8.50 (s, 1 H) | 0.000539 | 81459 |
| P63 | Cl | CONH₂ | CH₂CH₂CH₂F | cyclopropyl | C—F | ¹H NMR (400 MHz, DMSO-d₆) δ ppm 0.84-0.94 (m, 2 H), 1.02-1.11 (m, 2 H), 1.18-1.31 (m, 2 H), 1.44-1.64 (m, 2 H), 2.88-2.96 (m, 1 H), 4.17-4.29 (m, 3 H), 4.37 (t, J = 5.9 Hz, 1 H), 5.57 (s, 2 H), 6.85-6.95 (m, 1 H), 7.20 (dd, J = 8.7, 4.6 Hz, 1 H), 7.26 (dd, J = 8.8, 2.0 Hz, 1 H), 7.32 (dd, J = 9.4, 2.4 Hz, 1 H), 7.56 (d, J = 8.8 Hz, 1 H), 7.59-7.66 (m, 1 H), 7.77 (br. s., 1 H), 7.85 (d, J = 2.0 Hz, 1 H) | 0.001113 | >89869 |

TABLE 3-continued

| | R₁ | R₂ | R₃ | R₄ | X—R₅ | ¹H NMR | WT activity EC₅₀ (μM) | SI CC₅₀/EC₅₀ |
|---|---|---|---|---|---|---|---|---|
| P64 | Cl | CONHMe | CF₃-alkyl | cyclopropyl | N | ¹H NMR (400 MHz, DMSO-d₆) δ ppm 0.89 (m, 2 H), 1.09 (d, J = 5.8 Hz, 2 H), 1.34-1.48 (m, 2 H), 2.11-2.28 (m, 3 H), 2.84-2.98 (m, 4 H), 4.22-4.35 (m, 2 H), 5.59 (s, 2 H), 7.22-7.33 (m, 1 H), 7.63 (d, J = 9.0 Hz, 1 H), 7.82 (s, 1 H), 8.15 (d, J = 4.0 Hz, 1 H), 8.21 (d, J = 5.0 Hz, 1 H), 8.39 (s, 1 H) | 0.006416 | >3896 |
| P65 | Cl | CONH₂ | CF₃-alkyl | cyclopropyl | C—F | ¹H NMR (400 MHz, DMSO-d₆) δ ppm 0.83-0.93 (m, 2 H) 1.00-1.15 (m, 2 H) 1.30-1.46 (m, 2 H) 2.05-2.24 (m, 2 H) 2.83-2.93 (m, 1 H) 4.28 (t, J = 7.78 Hz, 2 H) 5.57 (s, 2 H) 6.84-6.95 (m, 1 H) 7.20 (dd, J = 8.53, 4.52 Hz, 1 H) 7.28 (dd, J = 8.78, 1.76 Hz, 1 H) 7.34 (dd, J = 9.29, 2.26 Hz, 1 H) 7.63 (d, J = 8.78 Hz, 1 H) 7.85 (d, J = 1.51 Hz, 1 H) | 0.001103 | >45348 |
| P66 | Cl | H | CF₃-alkyl | oxetanyl | N | NMR: 1H NMR (400 MHz, DMSO-d₆) δ ppm 1.50-1.71 (m, 4 H) 4.24-4.31 (m, 2 H) 4.34 (t, J = 5.65 Hz, 1 H) 4.45 (t, J = 5.90 Hz, 1 H) 4.94-5.01 (m, 2 H) 5.07 (t, J = 6.65 Hz, 2 H) 5.34 (s, 2 H) 5.53-5.62 (m, 1 H) 6.58 (s, 1 H) 7.13 (dd, J = 8.78, 2.01 Hz, 1 H) 7.50 (d, J = 8.78 Hz, 1 H) 7.53 (d, J = 5.27 Hz, 1 H) 7.56 (d, J = 2.01 Hz, 1 H) 8.29 (d, J = 5.27 Hz, 1 H) 8.45 (s, 1 H) | 0.00125 | 21581 |
| P67 | Cl | H | CF₃-alkyl | oxetanyl | N | 1H NMR (400 MHz, DMSO-d₆) δ ppm 1.63-1.78 (m, 2 H) 2.20-2.36 (m, 2 H) 4.28-4.40 (m, 2 H) 4.94-5.00 (m, 2 H) 5.06 (t, J = 6.50 Hz, 2 H) 5.35 (s, 2H) 5.51-5.62 (m, 1 H) 6.57 (s, 1 H) 7.16 (dd, J = 8.78, 2.01 Hz, 1 H) 7.48-7.61 (m, 3 H) 8.30 (d, J = 5.27 Hz, 1 H) 8.48 (s, 1 H) | 0.00125 | >85461 |
| P68 | Cl | CONH cyclopropyl | CF₃-alkyl | cyclopropyl | N | ¹H NMR (400 MHz, DMSO-d₆) δ ppm 0.67 (br. s., 2 H), 0.73 (m, 2 H), 0.89 (m, 2 H), 1.08 (d, J = 5.3 Hz, 2 H), 1.42 (m, 2 H), 2.18 (m, 2 H), 2.93 (m, 2 H), 4.28 (m, J = 7.0 Hz, 2 H), 5.54 (s, 2 H), 7.20-7.34 (m, 1 H), 7.25-7.28 (m, 1 H), 7.63 (d, J = 8.5 Hz, 1 H), 7.70 (br. s., 1 H), 8.23 (d, J = 4.3 Hz, 1 H), 8.36 (br. s., 1 H), 8.41 (br. s., 1 H) | 0.012589 | 249 |

TABLE 3-continued

| | $R_1$ | $R_2$ | $R_3$ | $R_4$ | $X-R_5$ | 1H NMR | WT activity $EC_{50}$ (μM) | SI $CC_{50}/EC_{50}$ |
|---|---|---|---|---|---|---|---|---|
| P69 | Cl | CONHMe | (CF3 group) | (CH2CF3) | N | 1H NMR(400 MHz, DMSO-d6) δ ppm 1.36-1.59 (m, 2 H) 2.17 (m, 2 H) 2.80-3.01 (m, 3 H) 4.29 (t, J = 7.50 Hz, 2 H) 4.90 (q, J = 7.50 Hz, 2 H) 5.67 (s, 2 H) 7.30 (d, J = 7.28 Hz, 1 H) 7.41 (d, J = 2.01 Hz, 1 H) 7.64 (d, J = 7.53 Hz, 1 H) 7.83 (s, 1 H) 8.07-8.22 (m, 1 H) 8.28 (d, J = 2.51 Hz, 1 H) 8.48 (s, 1 H) | | |
| P70 | Cl | CONH2 | (CF3 group) | (CH2CF3) | N | 1H NMR (400 MHz, DMSO-d6) δ ppm 1.38-1.54 (m, 2 H) 2.07-2.26 (m, 2 H) 4.28 (t, J = 6.90 Hz, 2 H) 4.90 (q, J = 9.03 Hz, 2 H) 5.70 (s, 2 H) 7.30 (d, J = 8.03 Hz, 1 H) 7.41 (d, J = 5.27 Hz, 1 H) 7.51-7.81 (m, 3 H) 7.87 (s, 1 H) 8.28 (d, J = 5.02 Hz, 1 H) 8.49 (s, 1 H) | | |
| P71 | CN | H | (CF3 group) | cyclopropyl | C—H | 1H NMR (400 MHz, DMSO-d6) δ ppm 0.85-0.94 (m, 2 H) 1.04-1.11 (m, 2 H) 1.67 (m, 2 H) 2.29 (m, 2 H) 2.92 (tt, J = 6.84, 3.45 Hz, 1 H) 4.40 (t, J = 7.78 Hz, 2 H) 5.29 (s, 2 H) 6.62 (s, 1 H) 7.03 (t, J = 7.53 Hz, 1 H) 7.09 (t, J = 7.53 Hz, 1 H) 7.21 (d, J = 7.53 Hz, 1 H) 7.25 (d, J = 7.53 Hz, 1 H) 7.51 (dd, J = 8.66, 1.38 Hz, 1 H) 7.71 (d, J = 8.53 Hz, 1 H) 8.05 (d, J = 1.00 Hz, 1 H) | | |
| P72 | Cl | H | (tBuOH) | cyclopropyl | N | 1H NMR (400 MHz, CHLOROFORM-d) δ ppm 0.98-1.07 (m, 2 H), 1.12 (s, 6 H), 1.17 (d, J = 5.3 Hz, 2 H), 1.38-1.50 (m, 2 H), 1.65 (m, J = 8.0 Hz, 2 H), 2.94 (tdd, J = 7.0, 7.0, 3.6, 3.5 Hz, 1 H), 4.21 (t, J = 7.8 Hz, 2 H), 5.22 (s, 2 H), 6.59 (s, 1 H), 7.11-7.16 (m, 2 H), 7.20 (d, J = 8.7 Hz, 1 H), 7.54 (d, J = 1.8 Hz, 1 H), 8.29 (d, J = 5.3 Hz, 1 H), 8.37 (s, 1 H) | 0.001585 | 24273 |
| P73 | Cl | H | (tBuOH) | oxetane | N | 1H NMR (400 MHz, CHLOROFORM-d) δ ppm 1.11 (s, 5 H), 1.36-1.49 (m, 2 H), 1.66 (m, J = 7.78, 7.78 Hz, 2 H), 4.19 (t, J = 7.78 Hz, 2 H), 5.04-5.18 (m, 4 H), 5.25 (s, 2 H), 5.53-5.70 (m, 1 H), 6.58 (s, 1 H), 7.13 (dd, J = 8.50, 1.80 Hz, 1 H), 7.19 (d, J = 8.50 Hz, 1 H), 7.53 (d, J = 1.51 Hz, 1 H), 7.59 (d, J = 5.27 Hz, 1 H), 8.35 (d, J = 5.27 Hz, 1 H), 8.46 (s, 1 H) | 0.003162 | 15070 |

TABLE 3-continued

| | R₁ | R₂ | R₃ | R₄ | X—R₅ | ¹H NMR | WT activity EC₅₀ (μM) | SI CC₅₀/EC₅₀ |
|---|---|---|---|---|---|---|---|---|
| P74 | Cl | H | (CH₂ chain with C(CH₃)₂OH) | CH₂CF₃ | N | ¹H NMR (400 MHz, CHLOROFORM-d) δ ppm 1.12 (s, 6 H), 1.36-1.49 (m, 2H), 1.55-1.71 (m, 2H), 4.17 (t, J = 7.78 Hz, 2 H), 4.51 (q, J = 8.53 Hz, 2 H), 5.30 (s, 2 H), 6.61 (s, 1 H), 7.02 (d, J = 5.27 Hz, 1 H), 7.15 (dd, J = 8.30, 2.00 Hz, 1 H), 7.20 (d, J = 8.30 Hz, 1 H), 7.55 (d, J = 2.01 Hz, 1 H), 8.35 (d, J = 5.52 Hz, 1 H), 8.44 (s, 1 H) | 0.003162 | 15708 |
| P75 | Cl | H | (CH₂)₃S(O)₂CH₃ | oxetanyl | C—F | ¹H NMR (400 MHz, DMSO-d₆) δ ppm 1.94 (br. s., 2 H), 2.96 (s, 3 H), 3.07-3.20 (m, 2 H), 4.39 (t, J = 7.40 Hz, 2 H), 4.90-5.02 (m, 2 H), 5.07 (t, J = 6.53 Hz, 2 H), 5.30 (s, 2 H), 5.55 (m, J = 6.40, 6.40 Hz, 1 H), 6.47 (s, 1 H), 6.91-7.06 (m, 1 H), 7.16 (dd, J = 8.91, 1.38 Hz, 1 H), 7.26 (dd, J = 8.78, 2.01 Hz, 1 H), 7.43-7.61 (m, 3 H) | | |
| P79 | Cl | H | (CH₂)₃CN | cyclopropyl | C—F | ¹H NMR (400 MHz, DMSO-d₆) δ ppm 0.88-0.94 (m, 2 H) 1.02-1.09 (m, 2 H) 1.80-1.92 (m, 2 H) 2.55 (t, J = 7.40 Hz, 2 H) 2.86-3.01 (m, 1 H) 4.31 (t, J = 7.65 Hz, 2 H) 5.24 (s, 2 H) 6.37 (s, 1 H) 6.92 (dq, J = 9.00, 2.50 Hz, 1 H) 7.15 (td, J = 9.29, 2.26 Hz, 2 H) 7.22 (dd, J = 8.53, 4.77 Hz, 1 H) 7.51 (d, J = 8.78 Hz, 1 H) 7.54 (d, J = 2.01 Hz, 1 H) | | |
| P80 | Cl | H | (CH₂)₃COOH | cyclopropyl | N | ¹H NMR (400 MHz, DMSO-d₆) δ ppm 0.82-0.96 (m, 2 H) 1.00-1.12 (m, 2 H) 1.46-1.67 (m, 2 H) 1.88-2.05 (m, 2 H) 2.91-3.04 (m, 1 H) 4.19 (t, J = 7.50 Hz, 2 H) 5.30 (s, 2 H) 6.40 (s, 1 H) 7.09 (dd, J = 8.53, 1.76 Hz, 1 H) 7.26 (d, J = 5.27 Hz, 1 H) 7.52 (d, J = 2.01 Hz, 1 H) 7.57 (d, J = 8.78 Hz, 1 H) 8.23 (d, J = 5.02 Hz, 1 H) 8.35 (s, 1 H) | | |
| P81 | Cl | H | (CH₂)₃S(O)₂CH₃ | oxetanyl | C—H | | | |

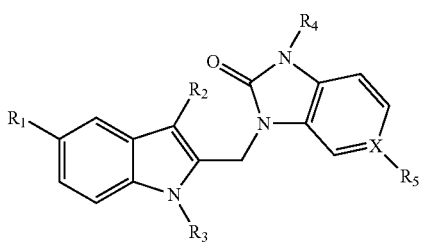

TABLE 4

| | R₁ | R₂ | R₃ | R₄ | X—R₅ |
|---|---|---|---|---|---|
| P82<br>P83<br>P84 | Cl | CONH₂ | (chain with SO₂CH₃) | cyclopropyl | N<br>CH<br>CF |
| P85<br>P86<br>P87 | Cl | CONH₂ | (chain with C≡N) | cyclopropyl | N<br>CH<br>CF |
| P88<br>P89<br>P90 | Cl | CONH₂ | (chain with C(CH₃)₂OH) | cyclopropyl | N<br>CH<br>CF |
| P91<br>P92<br>P93 | Cl | CONH₂ | (chain with SO₂CH₃) | CF₂CH₂— group | N<br>CH<br>CF |
| P94<br>P95<br>P96 | Cl | CONH₂ | (chain with C≡N) | CF₂CH₂— group | N<br>CH<br>CF |
| P97<br>P98<br>P99 | Cl | CONH₂ | (chain with C(CH₃)₂OH) | CF₂CH₂— group | N<br>CH<br>CF |
| P100<br>P101<br>P102 | Cl | CONH₂ | isobutyl chain | CF₂CH₂— group | N<br>CH<br>CF |

TABLE 4-continued

| | R₁ | R₂ | R₃ | R₄ | X—R₅ |
|---|---|---|---|---|---|
| P103<br>P104<br>P105 | Cl | CONH₂ | isobutyl chain | cyclopropyl | N<br>CH<br>CF |

The invention claimed is:

1. A compound of formula I, N-oxide, addition salt, quaternary amine, or a stereochemically isomeric form thereof;

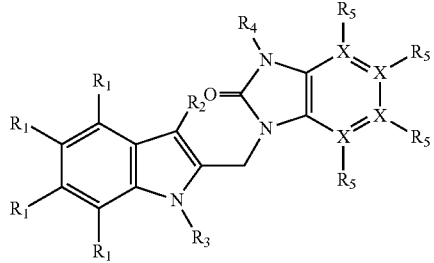

formula I wherein each X independently is C or N;
each R₁ is independently selected from the group consisting of H, halogen, $C_1$-$C_6$alkoxy, —$CF_3$, and $OCF_3$;
R₂ is selected from the group consisting of H, halogen, $C_1$-$C_6$alkyl, $C_3$-$C_7$cycloalkyl, $C_1$-$C_6$alkoxy, and $CO(R_7)$;
R₃ is —$(CR_8R_9)_n$—$R_{10}$;
R₄ is selected from the group consisting of H, $C_1$-$C_{10}$alkyl, $C_3$-$C_7$cycloalkyl, $C_2$-$C_{10}$alkenyl, $SO_2$—$R_8$, $CH_2CF_3$, $SO_2CH_3$ or a 4 to 6 membered saturated ring containing an oxygen atom;
R₅ is present where X is C, and is independently selected from the group consisting of H, $C_1C_6$alkyl, $C_3$-$C_7$cycloalkyl, $C_1$-$C_6$alkoxy, $CO(R_7)$, $CF_3$ and halogen;
R₅ is absent where X is N;
R₇ is selected from the group consisting of OH, $O(C_1$-$C_6$alkyl), $NH_2$, $NHSO_2N(C_1$-$C_6$alkyl)$_2$, $NHSO_2NHCH_3$, $NHSO_2(C_1$-$C_6$alkyl), $NHSO_2(C_3$-$C_7$cycloalkyl), and $N(C_1$-$C_6$-alkyl)$_2$, $NR_8R_9$, $NR_9R_{10}$;
n is an integer from 2 to 6;
R₈ and R₉ are each independently chosen from H, $C_1$-$C_{10}$alkyl, $C_3$-$C_7$cycloalkyl or R₈ and R₉ taken together form a 4 to 6 membered aliphatic ring that optionally contains one or more heteroatoms selected from the group N, S, O;
R₁₀ is selected from the group consisting of H, $C_1$-$C_6$alkyl, OH, CN, F, $CF_2H$, $CF_3$, $C(=NOH)NH_2$, $CONR_8R_9$, $COOR_8$, $CONR_8SO_2R_9$, $CON(R_8)SO_2N(R_8R_9)$, $NR_8R_9$, $NR_8COOR_9$, $OCOR_8$, $NR_8SO_2R_9$, $SO_2NR_8R_9$, $SO_2R_8$ or a 4 to 6 membered saturated ring containing an oxygen atom.

2. A compound according to claim 1, wherein
R₄ is selected from the group consisting of H, $C_1$-$C_{10}$alkyl, $C_3$-$C_7$cycloalkyl, $C_2$-$C_{10}$alkenyl, $SO_2$—$R_8$, or a 4 to 6 membered saturated ring containing an oxygen atom.

3. A compound according to claim 1 wherein each $R_1$ is independently selected from the group consisting of H, and halogen.

4. A compound according to claim 1, wherein $R_1$ in the para position to N—$R_3$ is selected from the group consisting of H, halogen, and all other $R_1$ are H.

5. A compound according to claim 4, wherein $R_1$ in the para position to N—$R_3$ is selected from the group consisting of bromo and chloro.

6. A compound according to claim 1, wherein $R_2$ is selected from the group consisting of H, halogen, and $CO(R_7)$.

7. A compound according to claim 1, wherein $R_2$ is selected from the group consisting of H, I, and $CONH_2$.

8. A compound according to claim 1, wherein $R_3$ comprises a —$(CR_8R_9)_n$— chain wherein $R_8$ and $R_9$ are H and n is 2-4.

9. A compound according to claim 1, wherein $R_{10}$ is selected from the group consisting of F, $CF_3$, OH, $SO_2R_8$, and CN, with $R_8$ being methyl.

10. A compound according to claim 1, wherein $R_4$ is $C_3$-$C_7$cycloalkyl or $CH_2CF_3$.

11. A compound according to claim 1, wherein $R_4$ is isopropyl.

12. A compound according to claim 1, wherein $R_4$ is oxetan-3-yl.

13. A compound according to claim 1, wherein the X in para position to N—$R_4$ is C and the $R_5$ on that X is F.

14. A compound according to claim 1, wherein one X is N and the other X's are C, the N being in para position to N—$R_4$.

15. A compound according to claim 1, wherein at most one $R_5$ is selected from the group consisting of $C_1$-$C_6$ alkyl, $C_1$-$C_6$-alkoxy, and halogen, and the other $R_5$ are H.

16. A compound according to claim 1, wherein all $R_5$ are H.

17. A pharmaceutical composition comprising a pharmaceutically acceptable carrier, and as active ingredient a therapeutically effective amount of a compound as claimed in claim 1.

18. A process for preparing a pharmaceutical composition, said process comprising intimately mixing a pharmaceutically acceptable carrier with a therapeutically effective amount of a compound as claimed in claim 1.

19. A compound according to claim 1, wherein the compound is

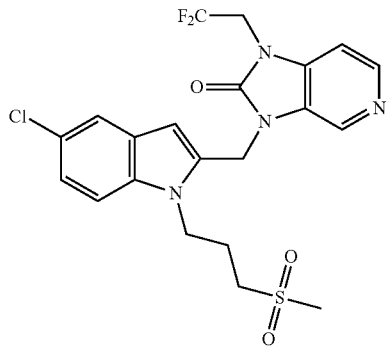

or N-oxide, addition salt, or quaternary amine thereof.

20. A compound of the formula

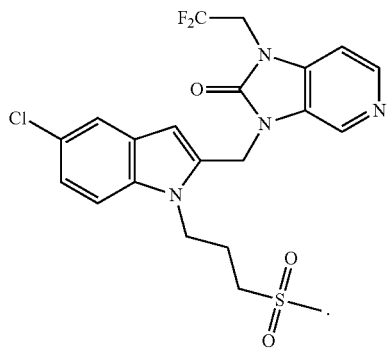

* * * * *

UNITED STATES PATENT AND TRADEMARK OFFICE
CERTIFICATE OF CORRECTION

PATENT NO. : 8,921,560 B2
APPLICATION NO. : 13/993200
DATED : December 30, 2014
INVENTOR(S) : Cooymans et al.

It is certified that error appears in the above-identified patent and that said Letters Patent is hereby corrected as shown below:

In The Claims

In claim 19 on column 76, line 6, please replace the structure with the following:

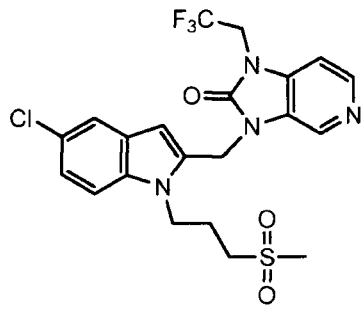

In claim 20 on column 76, line 25, please replace the structure with the following:

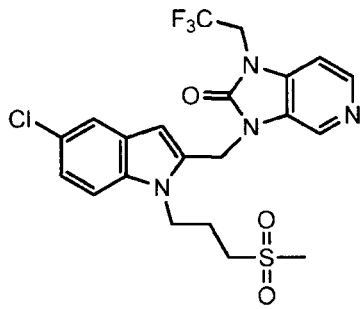

Signed and Sealed this
Twenty-second Day of September, 2015

Michelle K. Lee
*Director of the United States Patent and Trademark Office*